United States Patent [19]

Bennett et al.

[11] Patent Number: 5,693,815
[45] Date of Patent: Dec. 2, 1997

[54] PEPTIDES

[75] Inventors: Frank Bennett, Piscataway; Viyyoor M. Girijavallabhan, Parsippany; Naginbhai M. Patel, Piscataway, all of N.J.

[73] Assignee: Schering Corporation, Kenilworth, N.J.

[21] Appl. No.: 491,854

[22] PCT Filed: Jan. 14, 1994

[86] PCT No.: PCT/US94/00330

§ 371 Date: Jul. 14, 1995

§ 102(e) Date: Jul. 14, 1995

[87] PCT Pub. No.: WO94/17096

PCT Pub. Date: Aug. 4, 1994

Related U.S. Application Data

[63] Continuation-in-part of Ser. No. 140,808, Oct. 21, 1993, abandoned, which is a continuation-in-part of Ser. No. 6,086, Jan. 19, 1993, abandoned.

[51] Int. Cl.$^6$ .................. C07D 215/04; C07D 215/20
[52] U.S. Cl. .................................... 546/157; 546/155
[58] Field of Search ........................ 546/157, 155

[56] References Cited

FOREIGN PATENT DOCUMENTS

| | | |
|---|---|---|
| 310 918 | 4/1989 | European Pat. Off. . |
| 0 346 847 | 12/1989 | European Pat. Off. . |
| 0 386 611 | 9/1990 | European Pat. Off. . |
| 0 401 676 | 12/1990 | European Pat. Off. . |
| 0 526 009 | 2/1991 | European Pat. Off. . |
| 0 432 694 | 6/1991 | European Pat. Off. . |
| 0 432 695 | 6/1991 | European Pat. Off. . |
| 92/00750 | 1/1992 | WIPO . |
| 93/04043 | 3/1993 | WIPO . |

OTHER PUBLICATIONS

Journal of Organic Chemistry vol. 59, p. 3656 (1994).
Abstract S039 of The Journal of Biochemistry, Suppl. 18D, p. 130, 1994.
Science, vol. 248, pp. 358–361, Roberts et al. Rational Design of Peptide-Based HIV Proteinase Inhibitors (Apr. 1990).
Bolis et al. J. Med Chem. (1987) 30(10), 1729–1737.
Medicinal Chemistry, 3rd ed., A Burger, ed (Wiley–Interscience 1970) 1021–1052.
Burger's Medicinal Chemistry, 4th Ed M.E. Wolff, ed. (Wiley–Interscience 1981) 288–289.
Kokobu et al, Biochem Pharm, vol. 22, pp. 3217–3223(1973).
Medicinal Chemistry 23 ed. A. Burger, ed. (Wiley–Interscience 1960) 565–601.
Greenlee, Pharm. Res., vol. 4 (1087), pp. 364–374.
Repine et al J. Med Chem (1991) 34, 1935–1943.
ASM News vol. 56 No. 7 (Jul. 1990) 368.
Plattner et al., J. Med Chem, 31(12) pp. 2277–2288 (1988).

*Primary Examiner*—C. Warren Ivy
*Assistant Examiner*—D. Margaret M. Mach
*Attorney, Agent, or Firm*—Matthew Boxer; John J. Maitner

[57] ABSTRACT

Compounds of formula $$\text{Ar} \diagdown_{W} \diagdown_{N}^{Z} \diagup \underset{Q}{\overset{O}{\|}} \diagdown_{N}^{R_1} \diagdown_{U} O-L \qquad I$$

wherein Ar, W, Z, Q, $R_1$, U, and L are as set forth herein, are described. These compounds are active as agents against HIV and inhibit renin and therefore are also active against hypertension. Similar retroviruses against which the compounds of the invention are active include the retrovirus which causes feline AIDS, and the retrovirus which causes Rous' sarcoma which is a disease of chickens.

10 Claims, No Drawings

PEPTIDES

The present application is the United States national application corresponding to International Application No. PCT/US 94/00330, filed Jan. 14, 1994 and designating the United States, which PCT application is in turn a continuation-in-part of U.S. application Ser. No. 08/140,808, filed Oct. 21, 1993, now abandoned, the benefit of which applications are claimed pursuant to the provisions of 35 U.S.C. 120, 363 and 365 (C) which in turn is a continuation-in-part of U.S. application Ser. No. 08/006,086, filed Jan. 19, 1993 now abandoned.

SUMMARY OF THE INVENTION

The invention relates to compounds of the formula

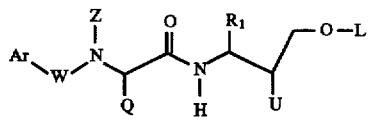
I wherein Ar is

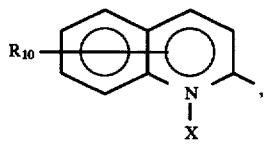

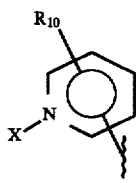

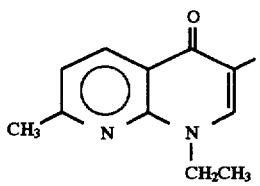

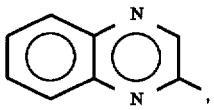

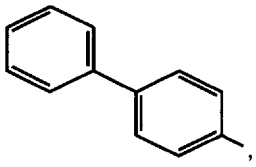

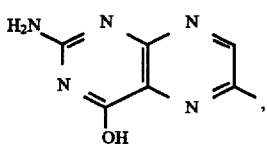

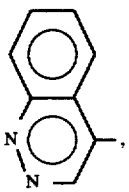

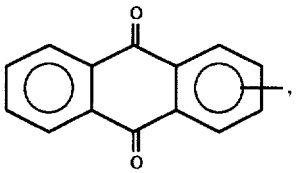

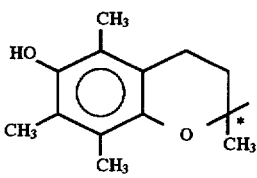

* indicates a mixture of isomers at this carbon

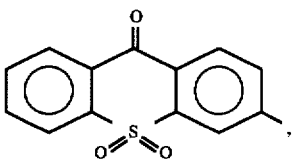

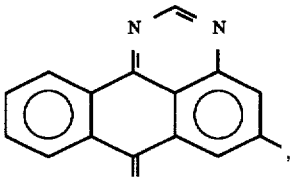

or

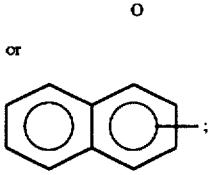

$R_{10}$ is H or OH;
X is O or an electron pair;
W is

or

Q is

CONH$_2$,

-continued
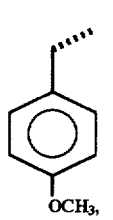
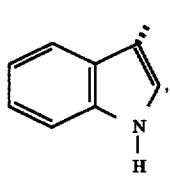
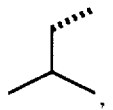
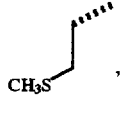
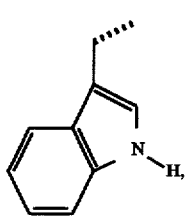
-continued
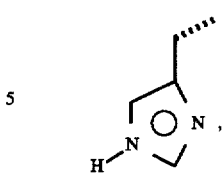
or
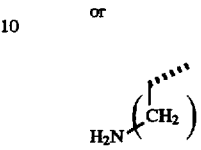
n is 0 to 4:
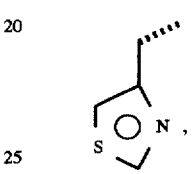
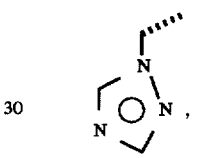
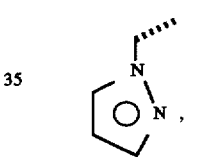
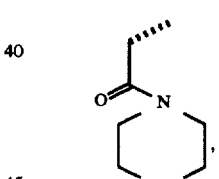
or
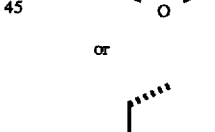
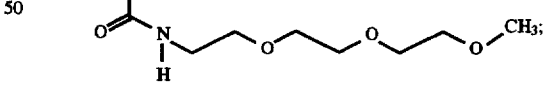
$R_1$ is
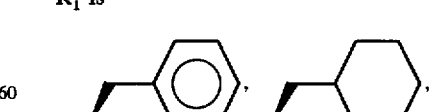
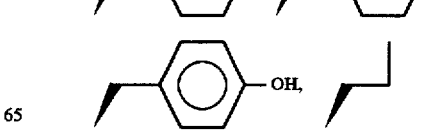

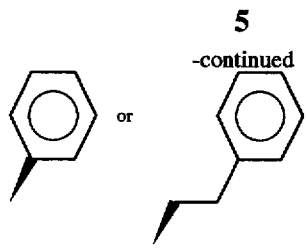 or

Z is H or Z and Q taken together are —(CH$_2$)$_3$— or —(CH$_2$)$_4$—

U is

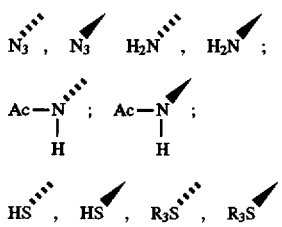

R$_3$ is C$_{1-11}$-alkyl or

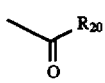

wherein R$_{20}$ is H or C$_{1-10}$-alkyl; and Ac is formyl or

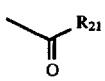

wherein R$_{21}$ is C$_{1-10}$ alkyl;

L is

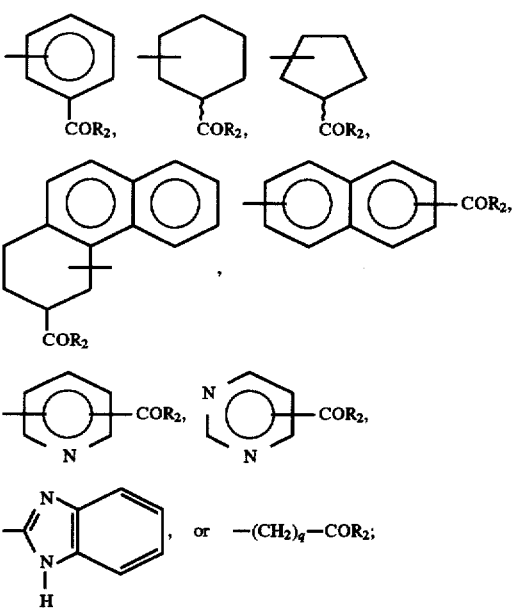

R$_2$ is

—O—C$_1$-C$_{12}$ alkyl, —O—(CH$_2$)$_m$Ph,

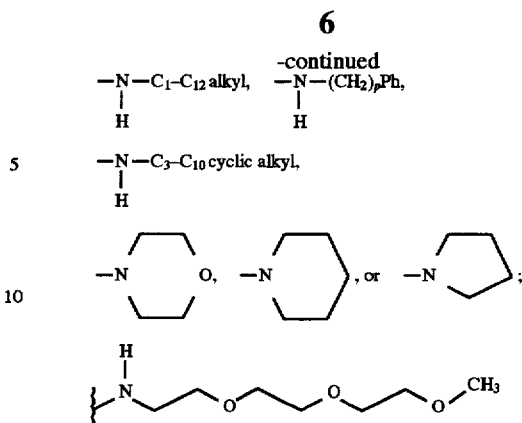

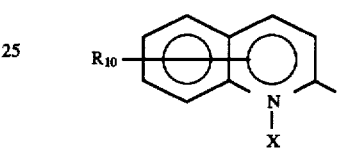

m is 0, 1 or 2;
p is 0, 1, or 2; and
q is 0, 1, or 2;
an epimer or racemate thereof, or a pharmaceutically acceptable salt thereof.

Preferred are compounds of formula I wherein Ar is

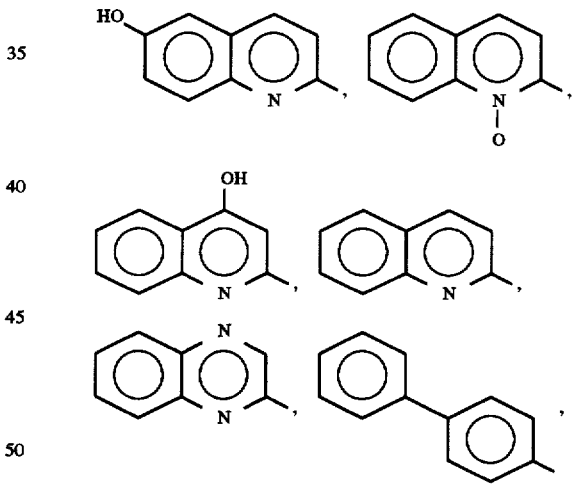

Among these the preferred compounds are those wherein Ar is

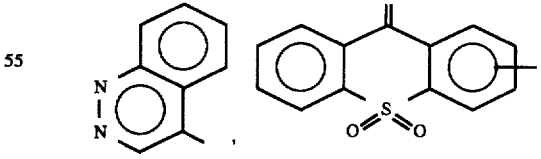
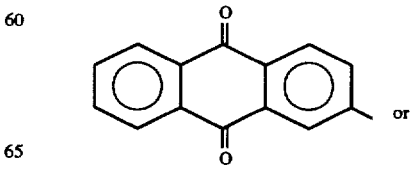
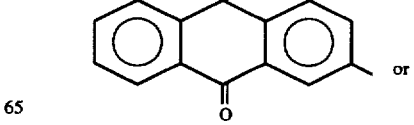
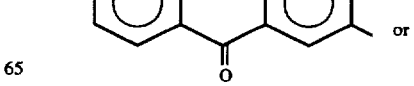
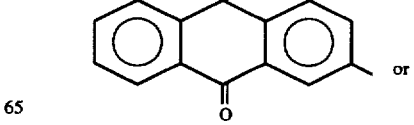

-continued

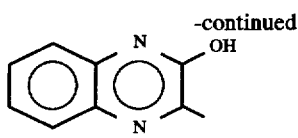

Also preferred are compounds of formula I wherein Ar is

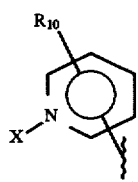

Preferred among the just above mentioned compounds are those wherein Ar is

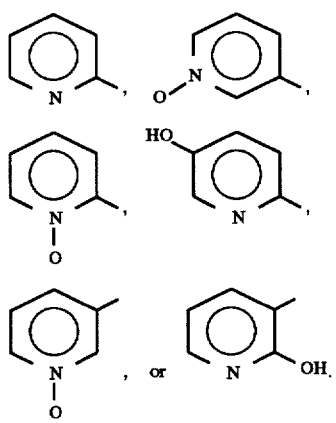

Most preferred are compounds wherein Ar is

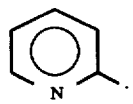

Also preferred are compounds of formula I wherein W is —$SO_2$— and —CO—. Most preferred are compounds of formula I wherein W is CO.

Also preferred are compounds of formula I wherein Q is

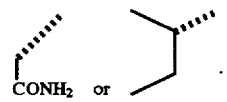

Most preferred are compounds of formula I wherein Q is

CONH$_2$.

Also preferred are compounds of formula I wherein $R_1$ is

Preferred are compounds of formula I wherein U is

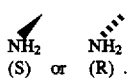
NH$_2$    NH$_2$
(S)  or  (R).

Most preferred are compounds of formula I wherein U is

NH$_2$
(S).

Preferred are compounds of formula I wherein —O-L is

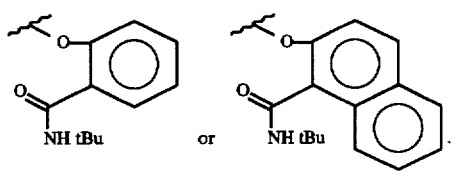

Most preferred are compounds of formula I wherein —O-L is

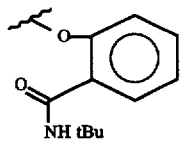

Most preferred are those compounds as described just above wherein $R_2$ is NH tBu or NHPh.

As used herein, alkyl denotes straight or branched saturated hydrocarbons which contain from 1 to 12 carbon atoms. Representative examples include methyl, butyl, isobutyl, isoamyl, and the like. Alternatively, the number of carbon atoms in a particular alkyl may be specified. For example, $C_1$–$C_7$ alkyl refers to an alkyl which may have one to seven carbon atoms.

Alkoxy denotes —O-alkyl wherein alkyl is as described above.

Ph denotes phenyl. Ms denotes mesyl. Halogen denotes chlorine, fluorine or bromine, and iodine.

As used herein, a bold faced line —■ denotes a bond that comes up above the plane of the page. A dashed line ⋯ denotes a bond that goes down below the plane of the page. A wavy line ~ denotes either racemic mixture or that the stereochemistry of this bond is not known.

Exemplary compounds of the invention include:

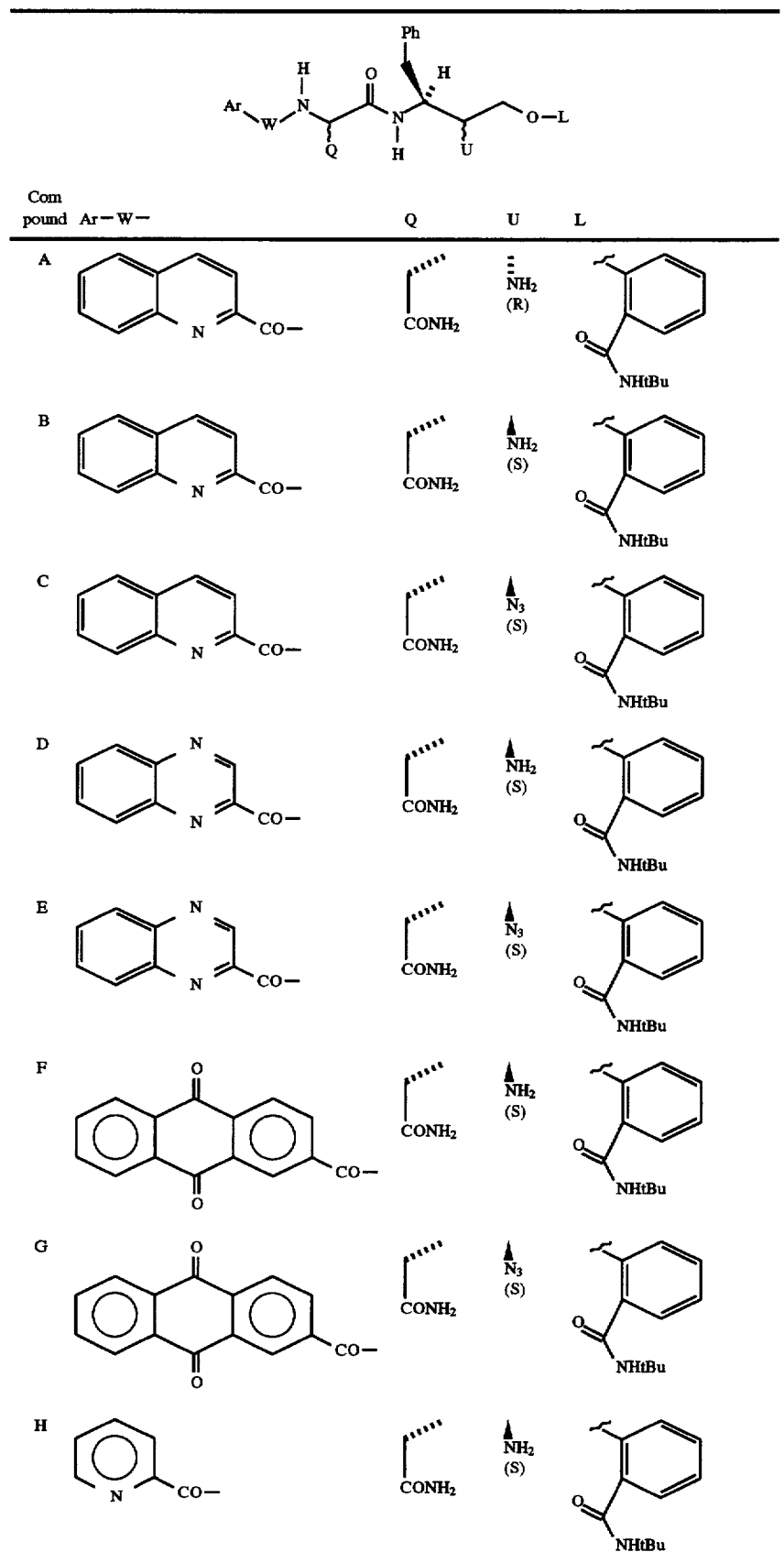

-continued

| Compound | Ar—W— | Q | U | L |
|---|---|---|---|---|
| I | pyridine-2-CO— | —CH₂CONH₂ | N₃ (S) | 2-(NHtBu)benzoyl |
| J | naphthalene-2-SO₂— | —CH₂CONH₂ | NH₂ (S) | 2-(NHtBu)benzoyl |
| K | naphthalene-2-SO₂— | —CH₂CONH₂ | N₃ (S) | 2-(NHtBu)benzoyl |
| L | biphenyl-4-CO— | —CH₂CONH₂ | NH₂ (S) | 2-(NHtBu)benzoyl |
| M | biphenyl-4-CO— | —CH₂CONH₂ | N₃ (S) | 2-(NHtBu)benzoyl |
| N | phthalazine-1-CO— | —CH₂CONH₂ | NH₂ (S) | 2-(NHtBu)benzoyl |
| O | phthalazine-1-CO— | —CH₂CONH₂ | N₃ (S) | 2-(NHtBu)benzoyl |
| P | quinoline-2-CO— | —CH₂CONH₂ | NHAc (S) | 2-(NHtBu)benzoyl |

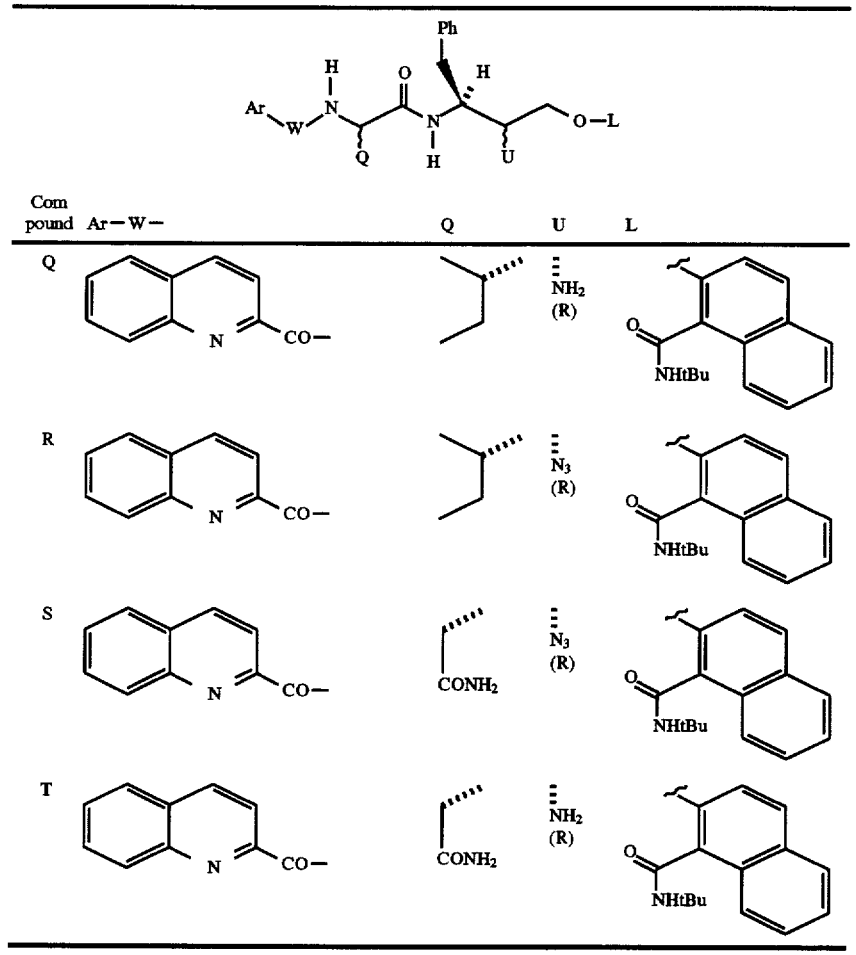

Other compounds of the invention are compounds of the formula U':

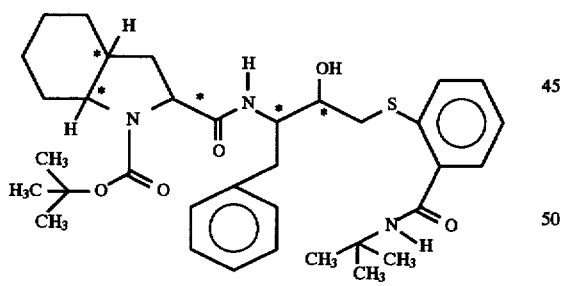

wherein * denotes all the possible stereoisomers at the particular carbon, and mixtures thereof or pharmaceutically acceptable salts thereof.

The chemical names for these compounds are 1-[(1,1-dimethylethoxy)carbonyl]-N-[3-[[2-[[(1,1-dimethylethyl)amino]carbonyl]phenyl]thio]-2(R and/or S)-hydroxy-1(R and/or S)-(phenylmethyl)-propyl]octahydroindole-2-carboxamide. The present invention includes within its scope, all possible stereoisomers of the formula U' set forth above.

A specific compound of the above formula is the following isomeric mixture, which is compound U:

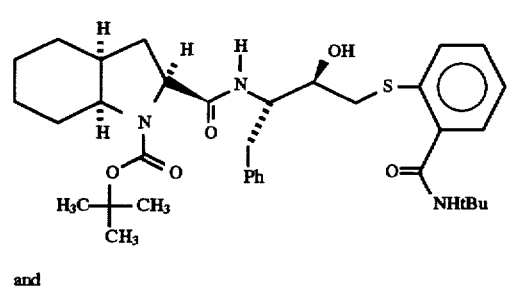

and

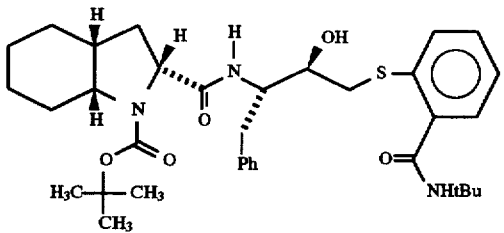

The most preferred compound of the invention is:

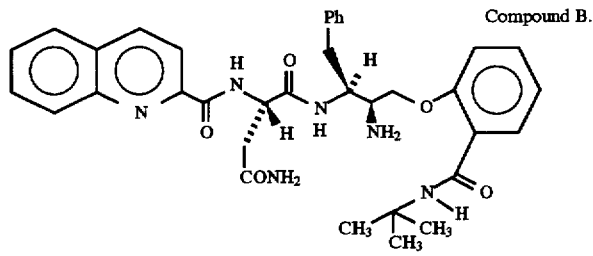

Compound B.

or a pharmaceutically acceptable salt thereof.

The chemical name for this compound is: $N^1$-[2-(S)-Amino-3-[[2-[[(1,1-dimethylethyl)amino]carbonyl]phenyl]oxy]-1(S)-(phenylmethyl)-propyl]-(S)-2-[[(2-quinolinyl)carbonyl]amino]-butanediamide The invention also relates to a pharmaceutical composition which comprises a compound of formula I in combination with a pharmaceutically acceptable carrier material.

The invention also relates to a method for treating AIDS which comprises administering to a patient in need of such treatment an anti-HIV effective amount of a compound of formula I.

The compounds of formula I, and all the other compounds of the invention, are also active against retroviruses including HIV; and also inhibit the action of renin and are therefore believed to active against hypertension.

Similar retroviruses against which the compounds of the invention are active include the retrovirus which causes feline AIDS, and the retrovirus which causes Rous' sarcoma which is a disease of chickens.

The two intermediate compounds shown just below are also active against retroviruses including HIV; and also inhibit renin and are therefore believed to active against hypertension. The synthesis of these intermediate compounds is set forth herein. These intermediate compounds are used in the preparation of compounds of formula I.

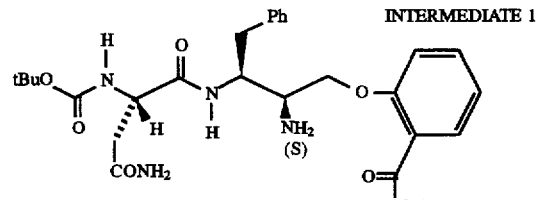

INTERMEDIATE 1

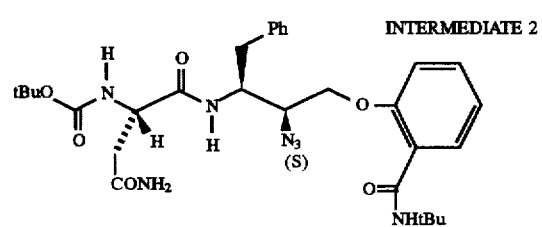

INTERMEDIATE 2

The numbering for these intermediate compounds is the same as that used in the table below. In the table below, "IN 1", for example means intermediate 1.

Other compounds of the invention have the following formulas:

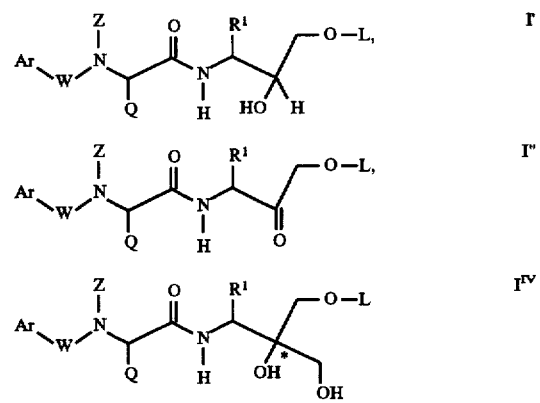

wherein * denotes a mixture of diastereomers at this position, and

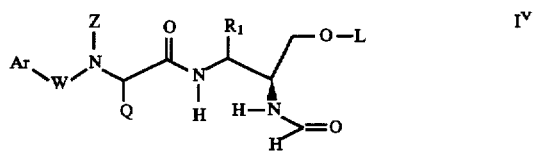

wherein Ar, W, Z, Q, $R_1$, and L are as described herein, or a pharmaceutically acceptable salt thereof.

Specific compounds which come within the above formulas are as follows:

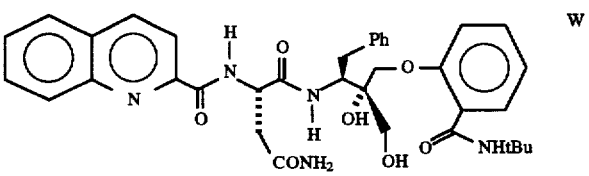

W

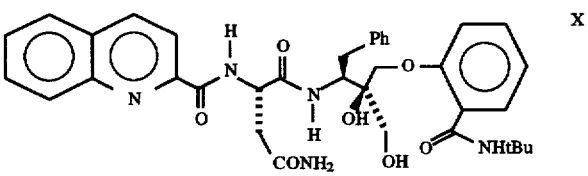

X

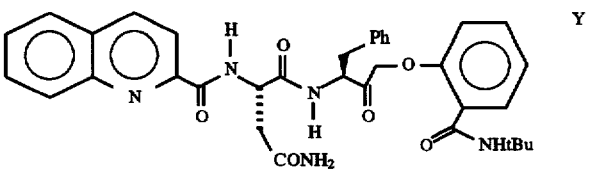

Y

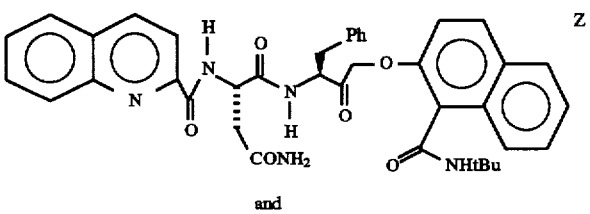

Z and

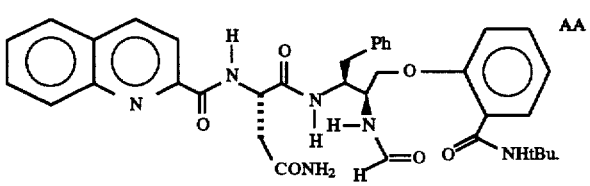

AA

DETAILED DESCRIPTION OF THE INVENTION

Asymmetric centers exist in compounds of formula I and other formulas of the invention. Accordingly, such compounds of formula I and other formulas include stereoisomers.

All such isomeric forms and mixtures thereof are within the scope of the present invention. Unless otherwise indicated, the methods of preparation may result in product distributions which include all possible structural isomers, although it is understood that physiological response may vary according to stereochemical structure. The isomers may be separated by conventional means such as fractional crystallization or HPLC (high performance liquid chromatography).

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

The compounds of formulas I form pharmaceutically acceptable salts. The preferred pharmaceutically acceptable salts are nontoxic, acid addition salts formed by adding to a compound of the invention about a stoichiometric amount of a mineral acid such as HCl, HBr, $H_2SO_4$, or $H_3PO_4$ or of an organic acid such as acetic acid, propionic, valeric, oleic, palmitic, stearic, lauric, benzoic, lactic, paratoluenesulfonic, methane sulfonic, citric, maleic, fumaric, succinic and the like, respectively.

The compounds of formula I may be prepared by the methods described below with reference to the Schemes 1, 2, 3, 4, 5, and 6. Compounds of formulas I', I", $I^{IV}$, and $I^V$ may be prepared by processes analogous to those set forth in the examples herein.

The compounds of formula (2) are known, or can be prepared in accordance with known methods, or else their preparation is described herein. For example, compounds of formula (2) include particular stereoisomers that may be prepared by means analogous to those set forth in DRUGS OF THE FUTURE 1991, 16(3) 210–212; J. Org. Chem., 1985, 50, 4615–4625; J. Org. Chem., 1987, 52 1487–1492; and J. Chem. Soc. Chem. Commun. 1992, 273–274, J. Chem. Soc. Chem. Commun. 1993, 737–738, or methods set forth in copending application PCT/US92/06525. These four publications and this patent application are herein incorporated by reference.

FORMULA SCHEME I

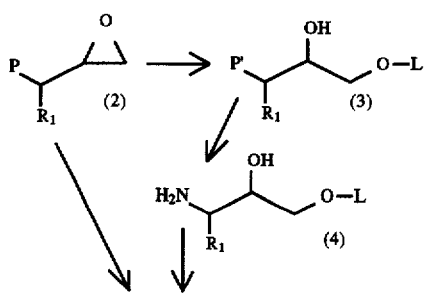

FORMULA SCHEME I

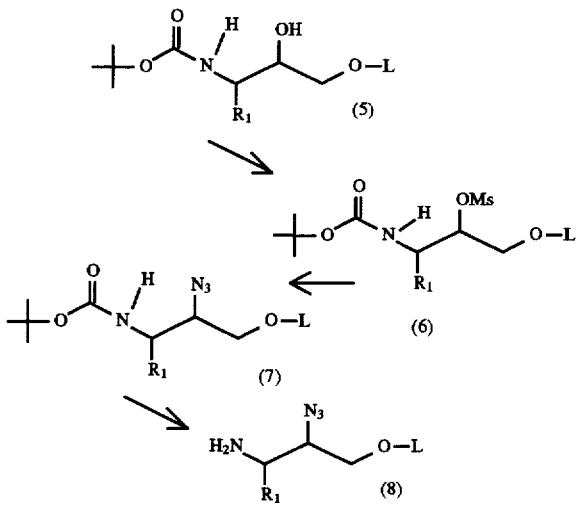

wherein, $R_1$, L, and Ms are as described herein, P is

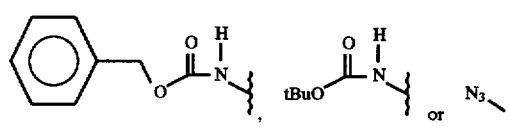

and P' is

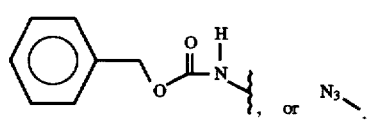

All reactions are carried out in an inert atmosphere such as nitrogen or argon unless otherwise stated.

A compound of formula (2) wherein and P is $PhCH_2OCONH$ or P is $N_3$, may be converted to a compound of formula (3) by reaction with a compound of the formula, H—O-L, in an organic solvent such as ethanol, dimethylsulfoxide (DMSO), or more preferably, dimethylformamide (DMF) at a temperature in the range of about 80° C. to about 200° C., more preferably, about 120° C. The resulting compound of formula (3) may be isolated by conventional means such as crystallization or chromatography, or it may be used directly in the next step of a synthesis of this invention to form a compound of formula (4). Compounds of the formula H—O-L are known or may be prepared in accordance with known methods.

A compound of formula (3) may be converted to a compound of formula (4) in an organic solvent such as methanol or more preferably ethanol in the presence of hydrogen and a catalyst such as 10% palladium on carbon. The reaction is carried out under about one atmosphere of hydrogen. The resulting compound of formula (4) may be isolated by conventional means such as crystallization or chromatography, or it may be used directly in the next step of a synthesis of this invention to form a compound of formula (5).

A compound of formula (4) may be converted to a compound of formula (5) in an organic solvent such as DMSO, DMF, or more preferably dioxane in the presence of di-tert-butyl dicarbonate and a base such as di-isopropylethylamine, or more preferably triethylamine at a temperature in the range of about 0° C. to about 35° C., more preferably about 25° C. The resulting compound of formula (5) may be isolated by conventional means such as crystallization or chromatography, or it may be used directly in the next step of a synthesis of this invention.

A compound of formula (2) wherein P is tBuOCONH, may be converted directly to a compound of formula (5) by reaction in an organic solvent such as ethanol, DMSO, or more preferably DMF with a compound of formula, H—O—L, at a temperature in the range of about 80° C. to about 200° C. more preferably at about 120° C. The resulting compound of formula (5) may be isolated by conventional means such as crystallization or chromatography, or it may be used directly in the next step of a synthesis of this invention.

A compound of formula (5) may be converted to a compound of formula (6) in the presence of methanesulfonyl chloride, in an organic solvent such as DMF, chloroform, or, more preferably dichloromethane in the presence of a base such as di-isopropylethylamine or more preferably triethylamine at a temperature in the range of about −10° C. to about 35° C., more preferably about 25° C. The resulting compound of formula (6) may be isolated by conventional means such as crystallization or chromatography, or it may be used directly in the next step of a synthesis of this invention.

A compound of formula (6) may be converted to a compound of formula (7) by treatment with sodium azide in an organic solvent such as DMSO or more preferably, DMF at a temperature in the range of about 50° C. to about 120° C., more preferably about 80° C. The resulting compound of formula (7) may be isolated by conventional means such as crystallization or chromatography, or it may be used directly in the next step of a synthesis of this invention to form a compound of formula (8).

A compound of formula (7) may be converted to a compound of formula (8) in the presence of trifluoroacetic acid in an organic solvent such as chloroform, or more preferably dichloromethane. The reaction is carried out at a temperature in the range of about 0° C. to about 35° C., more preferably about 25° C. The resulting trifluoroacetate salt may be subsequently treated with a base such as diisopropylethylamine or more preferably triethylamine at a temperature in the range of about 0° C. to about 35° C., more preferably about 25° C. The resulting free amine of formula (8) may be isolated by conventional means such as crystallization or chromatography, or it may be used directly in the next step of a synthesis of this invention to form a compound of formula (11) or (9) as shown in Formula Scheme 2.

FORMULA SCHEME 2

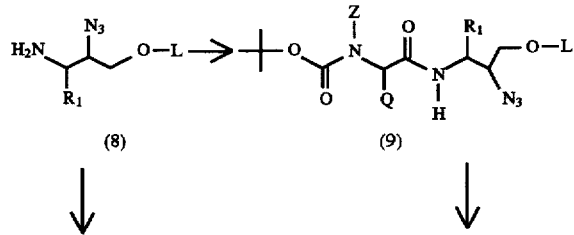

FORMULA SCHEME 2
-continued

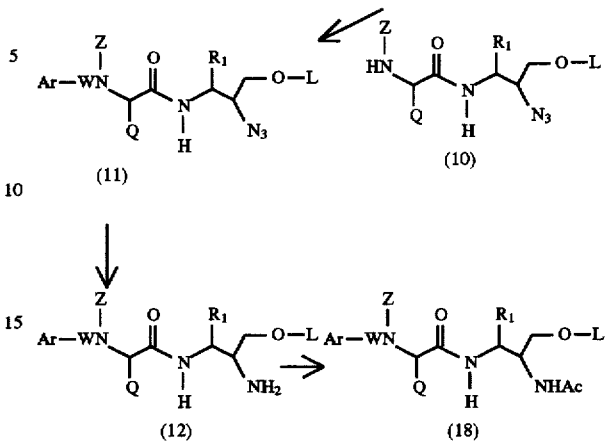

wherein $R_1$, L, Q, Ar, Z, and W are as described herein.

A compound of formula (8) may be converted to a compound of formula (9) in the presence of an active ester or mixed anhydride of the formula

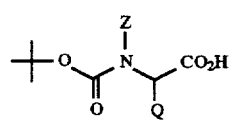

wherein Q is as described above in an appropriate solvent such as $CHCl_3$ or $CH_2Cl_2$. The active mixed anhydride of the acid of formula

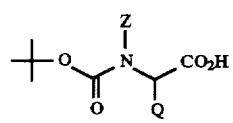

wherein Q is as described above is made by reacting the acid with benzotriazol-1-yloxy tris (dimethylamino) phosphonium hexafluorophosphate (BOP reagent) in an organic solvent such as $CHCl_3$ or $CH_2Cl_2$ in the presence of a base such as di-isopropylethylamine or more preferably triethylamine at a temperature in the range of about −20° C. to about 35° C., more preferably about 25° C.

The mixed anhydride of the acid of formula

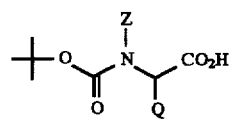

wherein Q is as described above can be made by conventional means preferably as pivaloyl mixed anhydride. (The pivaloyl mixed anhydride is made as follows: Pivaloyl chloride and the acid is reacted in the presence of a base such as triethylamine at a temperature in the range of about 0° C. to about −60° C.)

The resulting compound of formula (9) may be isolated by conventional means such as crystallization or chromatography, or it may be used directly in the next step of a synthesis of this invention to form a compound of formula (10).

A compound of formula (9) may be converted to a compound of formula (10) in the presence of trifluoroacetic acid in an organic solvent such as chloroform, or more preferably dichloromethane. The reaction is carried out at a temperature in the range of about −20° C. to about 35° C., more preferably about 25° C., followed by treatment with an amine base such as di-isopropylethylamine or more preferably triethylamine. The resulting compound of formula (10) may be isolated by conventional means such as crystallization or chromatography, or it may be used directly in the next step of a synthesis of this invention.

A compound of formula (10) may be converted to a compound of formula (11), in the presence of an active ester or mixed anhydride or acid chloride of the acids, Ar—CO$_2$H or ArSO$_3$H.

The active ester or mixed anhydride of Ar—CO$_2$H can be made by reacting with BOP reagent in an organic solvent, preferably CHCl$_3$ or CH$_2$Cl$_2$ in the presence of a base such as triethylamine.

The mixed anhydride of ArCO$_2$H can be made by conventional means, preferably as pivaloyl mixed anhydride, using pivaloyl chloride in an organic solvent, preferably CHCl$_3$ or CH$_2$Cl$_2$ in the presence of a base such as triethylamine at a temperature in the range of about 0° C. to about −60° C.

The reaction of an acid chloride of the acids ArSO$_3$H or ArCO$_2$H and an amine of formula (10) is carried out in an organic solvent, preferably CHCl$_3$ or CH$_2$Cl$_2$ in the presence of a base such as triethylamine at a temperature in the range of about −20° C. to about 25° C.

The resulting compound of formula (11) may be isolated by conventional means such as crystallization or chromatography, or it may be used directly in the next step of a synthesis of this invention to produce a compound of formula (12).

Alternatively, a compound of formula (8) may be directly converted to a compound of formula (11). The reaction is carried out in the presence of an active ester or mixed anhydride of an acid the formula

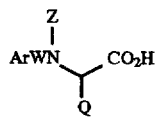

wherein Ar, W, Z and Q are as described above in an appropriate solvent, preferably CHCl$_3$ or CH$_2$Cl$_2$. using conditions analogous to those used in the conversion of a compound of formula (8) to a compound of formula (9).

The active ester or mixed anhydride of the formula

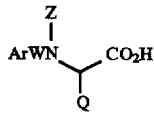

wherein Ar, W, Z and Q are as described above may be made by reacting the just above mentioned acid with BOP reagent in an organic solvent such as CHCl$_3$ or CH$_2$Cl$_2$ in the presence of a base such as triethylamine.

The mixed anhydride of

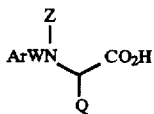

can be made by conventional means, preferably as pivaloyl mixed anhydride using pivaloyl chloride in an organic solvent like CH$_2$Cl$_2$ in the presence of a base such as triethylamine at a temperature in the range of about 0° C. to about −60° C. The resulting compound of formula (11) may be isolated by conventional means such as crystallization or chromatography, or it may be used directly in the next step of a synthesis of this invention to form a compound of formula (12).

A compound of formula (11) may be converted to a compound of formula (12) in an organic solvent such as methanol or more preferably ethanol in the presence of a catalyst such as 10% palladium on carbon. The reaction is carried out under 1 atmosphere of hydrogen.

The resulting compound of formula (12) may be isolated by conventional means such as crystallization or chromatography, or it may be used directly in the next step of a synthesis of this invention to form a compound of formula (18). A compound of formula (12) may be converted directly into a compound of formula (18) by reacting the amine of the formula (12) with an active ester or mixed anhydride or acid chloride of an acid.

The active ester or mixed anhydride of the acid is made by reacting the acid with BOP reagent in an organic solvent such as CH$_2$Cl$_2$ or CHCl$_3$ in the presence of a base such as triethylamine. The mixed anhydride can be made by conventional means, preferably as the pivaloyl mixed anhydride using pivaloyl chloride in an organic solvent such as CH$_2$Cl$_2$ in the presence of a base such as triethylamine at a temperature in the range of about 0° C. to about −60° C.

Also a compound of formula (12) may be converted to a compound of formula (18) by reaction with an acid chloride in an organic solvent such as CH$_2$Cl$_2$ or CHCl$_3$ in the presence of a base such as triethylamine at a temperature in the range of about −20° C. to about 35° C.

The resulting compound of formula (18) may be isolated by conventional means such as crystallization or chromatography.

FORMULA SCHEME 3

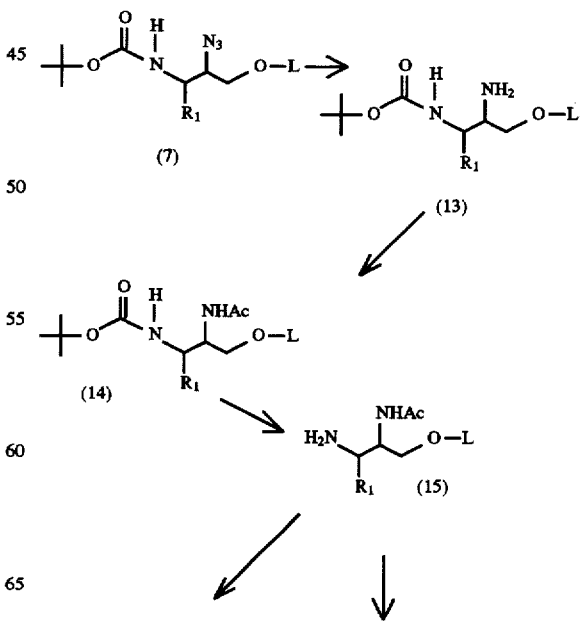

-continued
FORMULA SCHEME 3

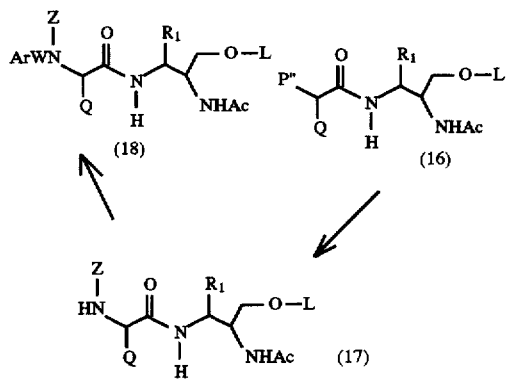

wherein $R_1$, L, Ac, Ar, W, P, Z and Q are as described herein and P" is

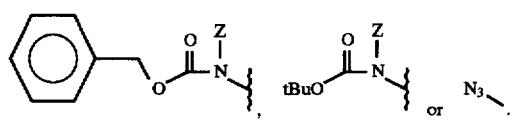

A compound of formula (7) may be converted to a compound of formula (13) in a manner similar to the hydrogenation described above for the conversion of a compound of formula (11) to a compound of formula (12). The resulting compound of formula (13) may be isolated by conventional means such as crystallization or chromatography, or it may be used directly in the next step of a synthesis of this invention to form a compound of formula (14).

A compound of formula (13) may be converted to a compound of formula (14) in presence of an active ester or mixed anhydride or acid chloride of an acid in an organic solvent such as $CHCl_3$ or $CH_2Cl_2$. The active ester or mixed anhydride is made by reacting the acid with benzotriazol-1-yloxytris(dimethylamino)phosphonium hexafluorophosphate (BOP reagent) in an organic solvent such as $CHCl_3$ or $CH_2Cl_2$ in the presence of a base such as triethylamine. The mixed anhydride of the acid can be made by conventional means, preferably as pivaloyl mixed anhydride using pivaloyl chloride in an organic solvent like $CH_2Cl_2$ in the presence of a base such as triethylamine at a temperature in the range of about −60° C. to about 35° C. The compound of formula (13) can also be converted to a compound of formula (14) in the presence of an acid chloride in an organic solvent such as $CHCl_3$ or $CH_2Cl_2$ in the presence of a base such as triethylamine at a temperature in the range of about −60° C. to about 25° C. The resulting compound of formula (14) may be isolated by conventional means such as crystallization or chromatography, or it may be used directly in the next step of a synthesis of this invention to form a compound of formula (15).

A compound of formula (14) may be converted to a compound of formula (15)in the presence of trifluoroacetic acid in an organic solvent such as $CH_2Cl_2$ or $CHCl_3$ at a temperature in the range of about 0° C. to about 35° C., preferably about 25° C., followed by treatment with triethylamine at a temperature in the range of about 0° C. to about 25° C. The resulting compound of formula (15) may be isolated by conventional means such as crystallization or chromatography, or it may be used directly in the next step of a synthesis of this invention to form a compound of formula (16) or formula (18).

A compound of formula (15) may be converted to a compound of formula (16) by reaction with an ester or mixed anhydride of the acid of the formula

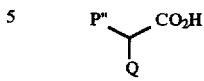

wherein P" is as described above, in an appropriate solvent, preferably $CHCl_3$ or $CH_2Cl_2$.

The active ester of

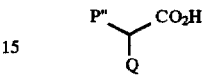

wherein P" is as described above, is made by reacting the just above mentioned acid with BOP reagent in an organic solvent preferably $CHCl_3$ or $CH_2Cl_2$ in the presence of a base such as triethylamine at a temperature in the range of about 0° C. to about −60° C.

The resulting compound of formula (16) may be isolated by conventional means such as crystallization or chromatography, or it may be used directly in the next step of a synthesis of this invention to form a compound of formula (17).

A compound of formula (16) may be converted to a compound of formula (17) by removing the protecting group. Where P" is $PhCH_2OCONZ$, or P" is $N_3$ (to obtain compounds of formula (17) where Z is H) removal is carried out in a solvent such as ethanol or methanol in the presence of a catalyst such as 10% Pd on carbon. The reaction is carried out under one atmosphere of hydrogen. Where P" is t-BOCNZ, t-BOC removal is carried out in a solvent such as $CHCl_3$ or $CH_2Cl_2$ in the presence of trifluoroacetic acid at a temperature in the range of about 0° C. to about 25° C. followed by treatment with a base such as triethylamine. The resulting compound of formula (17) may be isolated by conventional means such as crystallization or chromatography, or it may be used directly in the next step of a synthesis of this invention to produce a compound of formula (18).

A compound of formula (17) may be converted to a compound of formula (18) in the presence of an ester, mixed anhydride or acid chloride of the acids $ArCO_2H$ or $ArSO_3H$.

The active ester or mixed anhydride of $ArCO_2H$ is made by reacting the acid with BOP reagent in an organic solvent like $CH_2Cl_2$ or $CH_3Cl$ in the presence of a base such as triethylamine.

The mixed anhydride of $ArCO_2H$ can be made by conventional means, preferably as the mixed pivaloyl anhydride using pivaloyl chloride in an organic solvent like $CH_2Cl_2$ in the presence of a base such as triethylamine at about 0° C. to about −60° C.

Alternatively, a compound of formula (17) may be converted to a compound of formula (18) in the presence of an acid chloride of $ArCO_2H$ or $ArSO_3H$ in an organic solvent like $CH_2Cl_2$ or $CH_3Cl$ in the presence of a base such as triethylamine at about −20° C. to about 25° C.

Also a compound of formula (15) may be converted directly to a compound of formula (18) by reaction with an active ester or mixed anhydride of the formula

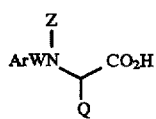

wherein Ar, W, Z and Q is as described above in a manner analogous to the conversion of a compound of formula (8) to a compound of formula (9) or (11).

FORMULA SCHEME 4

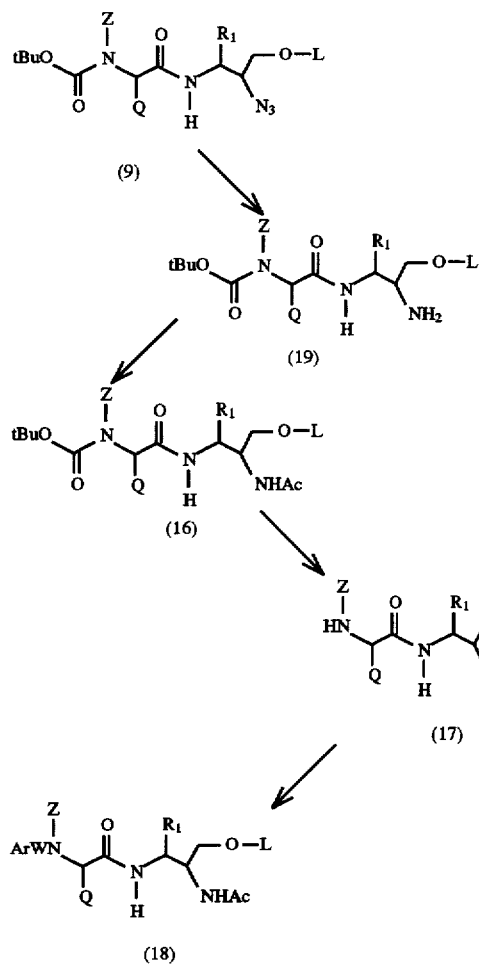

wherein Ar, W, Z, Q, $R_1$, Ac and L are as described above.

A compound of formula (9) may be converted to a compound of formula (19) by procedures similar to the hydrogenation described above wherein a compound of formula (11) is converted to a compound of formula (12). The resulting compound of formula (19) may be isolated by conventional means such as crystallization or chromatography, or used directly in the next step of the synthesis of this invention.

A compound of formula (19) may be converted to a compound of formula (16) by using procedures analogous to those described for the conversion of a compound of formula (12) into a compound of formula (18). A compound of formula (16) may be converted to compounds of formula (17 & 18) by procedures shown in Formula Scheme 3 where P" is tBOCNZ.

Compounds of formulas (9), (19) and (16) are also anti-AIDS (HIV) agents.

FORMULA SCHEME 5

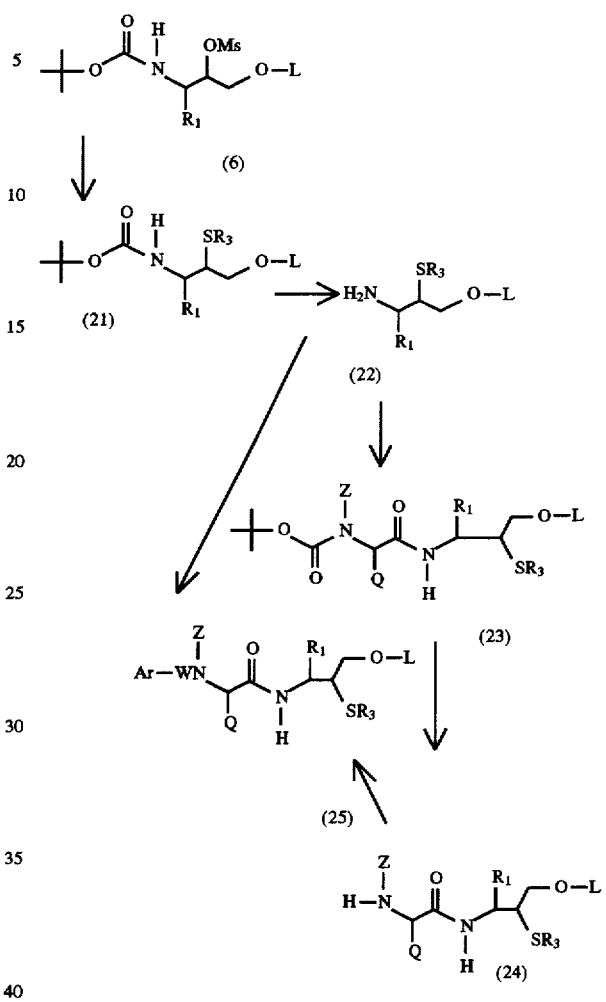

wherein $R_1$, L, $R_3$, Q, Ar, Z and W are as described herein.

A compound of formula (6) may be converted to a compound of formula (21) by reaction with a thiolate or a thiocarboxylate, such as potassium thiolacerate, in an organic solvent such as methanol, DMSO, or preferably ethanol at a temperature in the range of about $-10°$ C. to $80°$ C. more preferably $25°$ C. The resulting compound of formula (21) may be isolated by conventional means such as crystallization or chromatography or it may used directly in the next step of this invention to form a compound of formula (22).

A compound of formula (21) may be converted to a compound of formula (22) by methods analogous to the conversion of a compound of formula (7) to a compound of formula (8) as shown in Formula Scheme 1 herein.

Using procedures analogous to those shown in Formula Scheme 2 for the preparation of compounds of formulas (9), (10), and (11) from compounds of formula (8), compounds of formula (22) may be converted to compounds formulas (23), (24), and (25). By procedures analogous to the conversion of a compound of formula (8) to a compound of formula (11), a compound of formula (22) may be converted directly to a compound of formula (25).

FORMULA SCHEME 6

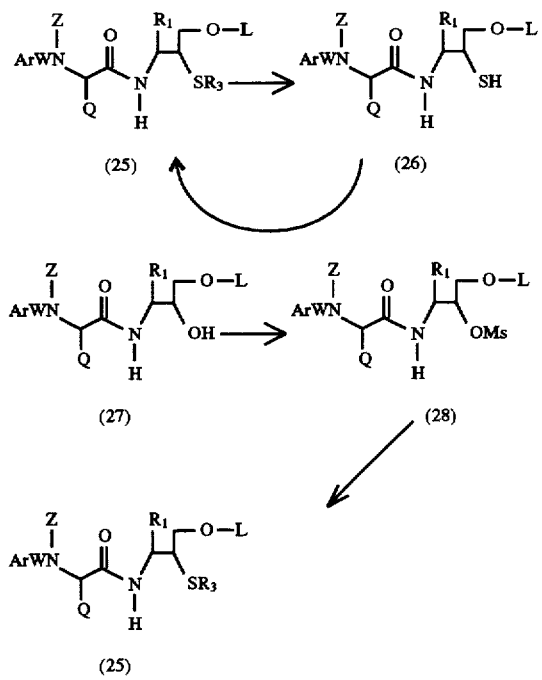

wherein Ar, W, R$_3$, L, R$_1$, Z and Q are as described herein.

A compound of formula (25), wherein R$_3$ is —COR$_{20}$, may be converted to a compound of formula (26) in organic solvent such as ethanol, methanol or water or a mixture of water and ethanol or methanol in the presence of a base such as sodium or potassium carbonate, or lithium, sodium or potassium hydroxide at a temperature in the range of about −10° C. to about 80° C. more preferably about 25° C. The resulting compound of formula (26) may be isolated by conventional means.

Using a procedure analogous to the conversion of a compound of formulas (12) to a compound of formula (18), a compound of formula (26) may be converted to compound of formula (25).

Using a procedure analogous to the conversion of a compound of formula (5) to a compound of formula (6), a compound of formula (27) may be converted to compound of formula (28).

Using a procedure analogous to the conversion of a compound of formula (6) to a compound of formula (21), a compound of formula (28) may be converted to compound of formula (25).

Compounds of formula (27) may be prepared by methods identical to or analogous to those set forth in copending application PCT/US92/06525, which is herein incorporated by reference.

While the formula schemes have been drawn using formulas that do not show stereochemistry for -U in the right hand moiety

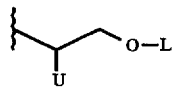

of the compounds, it will be understood that compounds with a specific stereochemistry on the -U bearing carbon can be made.

For example, where U is —N$_3$, —NH$_2$, —NHAc, —SH, or —SR$_3$, plate chromatography of a compound of formula

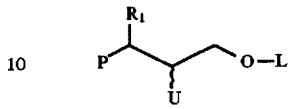

wherein P, R$_1$, U, and L are as described herein can be used to isolate a compound of formula

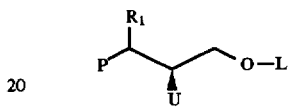

wherein P, R$_1$, U, and L are as described herein which may in turn be ultimately converted to a compound of formula I with the stereochemistry:

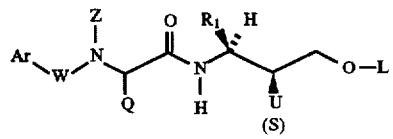

wherein Ar, W, Z, Q, R$_1$, U, and L are as described herein

Also ring opening of an epoxide of the formula

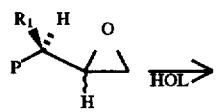

and subsequent acidification and chromatography results in the separation of hydroxy compounds of the formulas

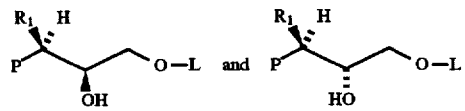

These hydroxy compounds can be used as shown in Formula Scheme 1 to obtain final products of corresponding stereochemistry.

Compounds of formulas (11), (12), (18), (25), and (26) in the formula schemes above fall within formula I. Moreover all of the compounds of formula I fall within one of formulas (11), (12), (18), (25), and (26).

Further compounds of the invention may be prepared as shown below.

Formula Scheme 7

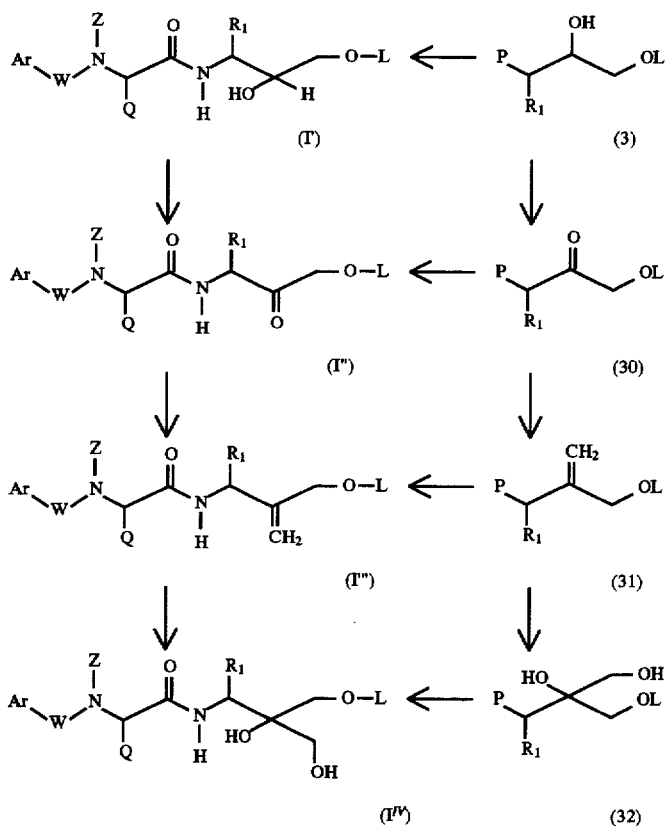

wherein Ar, W, Z, Q, R$_1$, L, and P are as described herein.

A compound of formula I' may be converted to a compound of formula I" by reaction with an oxidant such as dipyridine chromium trioxide complex or sodium dichromate or pyridinium dichromate in an organic solvent such as dichloromethane, dimethylformamide or pyridine at a temperature in the range of about 0°–100° C. The resulting compound of formula I", may be isolated by crystallization or chromatography or it may be used directly in the next step of a synthesis of this invention to form a compound of formula I"'.

A compound of formula I" may be converted to a compound of formula I"' in an organic solvent such as tetrahydrofuran or diethyl ether at a temperature in the range –78° to +35° C. under an inert atmosphere of nitrogen or argon. The reaction is carried out in the presence of methylenetriphenylphosphorane generated by the action of a strong base such as lithium, sodium or potassium hexamethyl disilazide or butyl lithium on methyltriphenyl phosphonium chloride, bromide or iodide. The resulting compound of formula I"' can be isolated by conventional means such as crystallization or chromatography or used in the next step of a synthesis of this invention for producing a compound of Formula.

A compound of formula I"' can be converted to a compound of formula I$^{IV}$ in an organic solvent such as butanol in the presence of water and osmium tetroxide or a combination of potassium osmate dihydrate, potassium ferricyanide and potassium carbonate at a temperature in the range of about –35° to 35°. Alternatively, this conversion can be carried out with AD-MIX-α or AD-MIX-β in the presence or absence of additional components such as chiral ligands which can be present in these mixtures. The compound of formula I$^{IV}$ may be isolated by conventional means such as crystallization or chromatography.

Using the procedure described above for the conversion of a compound of formula I' to a compound of formula I", a compound of formula 3 or formula 5 may be converted to a compound formula 30. The compound of formula 30 may be isolated by conventional means such as crystalization or chromatography or may be used directly in a synthetic step of this disclosure to prepare a compound of formula I", or used to prepare a compound of formula 31.

Using the procedures described for the conversion of a compound of formula 8 to a compound of formula 11, a compound of formula 30 can be converted to a compound of formula I".

Using the procedure described above for the conversion of a compound of formula I" to a compound of formula I"', a compound of formula 30 may be converted into a compound of formula 31.

Using the procedures described above for the conversion of formula 8, a compound of formula 11, a compound of formula 31 may be converted to a compound of formula I"'.

Using the procedures described above for the conversion of a compound of formula I"', to a compound of formula I$^{IV}$, a compound of formula 31 may be converted to a compound of formula 32

Using the procedures described above for the conversion of a compound of formula 8 to a compound of formula 11, a compound of formula 32 may be converted to a compound of formula I$^{IV}$.

The compounds of formula I are active against HIV proteinases, including HIV 1 proteinase. The compounds of formula I are active as agents for treating AIDS inasmuch as they are active against HIV. The compounds of formula I are active as agents for inhibiting renin.

The anti-HIV activity of the compounds of formula I can be shown by the following test protocol:

TEST 1—INHIBITION OF PROTEOLYTIC ACTIVITY OF HIV-1-PROTEASE

The ability of compounds of the invention to inhibit the proteolytic activity of HIV-1 protease can be determined by using the method of Louis, et al., *Biochem. Biophys. Res. Comm.* 159:87–94, (1989), which is herein incorporated by reference. In using the method of Louis et al., HIV Substrate III, His-Lys-Ala-Arg-Val-Leu-pNO$_2$Phe-Glu-Ala-Nle-Ser-NH$_2$ purchased from Bachem Bioscience, Inc. Philadelphia, Pa. can be used in place of the nonapeptide substrate Val-Ser-Gln-Asn-Tyr-Pro-Ile-Val-Gln-amide.

TEST 2—INHIBITION OF THE GROWTH OF HIV-1 IN TISSUE CULTURE CELLS (Cells)

This test measured the capability of the compounds to inhibit the growth of HIV-1 in tissue culture cells. CEM-SS cells (human T-lymphocyte derived tissue culture cells) were infected with HIV-1, isolate III B which was produced in tissue culture. After 7 days, the virus has killed the cells as monitored by extensive syncytia formation (cell fusion). The test measured the capability of the chemical synthetic compounds to prevent syncytia formation and cell death. CEM cells were grown at 37° C. in an atmosphere of 5% CO$_2$. HIV isolate III B was prepared by growth in and crude purification from CEM cells. The chemical synthetic compound was added to 96 well microtiter plates and diluted in varying steps across the wells of the plate. Cells and virus were added to each well and the concentration of the chemical synthetic compound required to inhibit syncytia formation by 50% (the IC$_{50}$) after 7 days was determined. The viability of CEM cells which are not infected with HIV-1 isolate III B was simultaneously determined by the MTT assay, as described in Mossman, *J. Immunolog. Methods* 65:55–63, 1983, which is herein incorporated by reference.

TEST 3—INHIBITION OF PROTEOLYTIC ACTIVITY OF HIV-1-PROTEASE AS DETERMINED BY SCINTILLATION PROXIMITY ASSAY (SPA)

This is an alternative assay to test #1 and is used to determine the ability of compounds to inhibit the HIV1 protease activity. The SPA assay for HIV1 protease has been developed by Amersham Corporation, Arlington Heights, Ill., and is available for commercial use. In this system the substrate for HIV1 protease, AcN-(I$^{125}$)Tyr-Arg-Ala-Arg-Val-Phe-Phe-Val-Arg-Ala-Ala-Lys-SPA bead, is cleaved by the HIV1 protease at the Phe-Phe bond releasing the I$^{125}$-labelled peptide fragment from the SPA bead. This event causes removal of detectable signal from the microsphere bead indicated by reduction in radioactivity (measured in CPM), which is proportional to the proteolytic activity. The substrate, and the HIV1 protease were incubated in presence of synthetic compound in various dilutions at room temperature for 40 minutes, and the concentration of the compound required to inhibit the proteolytic activity by 50% (IC$_{50}$) was determined.

IC$_{50}$'s in Test 1 (Protease Activity) and Test 2 (Anti-HIV) above, for a series of compounds of formulas I of the invention are shown in Table 1 below. Mass spectrum (MS) numbers are also shown Table 1. Compound letters correspond to the letters that were assigned above.

| Compound | Physcal Data | SPA IC$_{50}$ (nM) | Cells IC$_{50}$ (µg/ml) |
|---|---|---|---|
| IN 1 | FABMS, MH$^+$, 570 | >2000 nM | |
| IN 2 | FABMS, MH$^+$, 596 | >2000 nM | |
| A | FABMS, MH$^+$, 625 | 1350 nM | 1.8 |
| B | FABMS, MH$^+$, 625 | 1500,600 nM* | 1.4 |
| C | FABMS, MH$^+$, 651 | 1750 nM | |
| D | FABMS, MH$^+$, 626.3 | 990 nM | 0.88 |
| E | FABMS, MH$^+$, 653 | 30% at 2000 nM | |
| F | FABMS, MH$^+$, 704 | 700 nM | 5.2 |
| G | FABMS, MH$^+$, 730.4 | >2000 nM | |
| H | FABMS, MH$^+$, 575 | 20% at 2000 nM | |
| I | FABMS, MH$^+$, 601 | >2000 nM | |
| J | FABMS, MH$^+$, 660 | 29% at 2000 nM | |
| K | FABMS, MH$^+$, 686.7 | >2000 nM | |
| L | FABMS, MH$^+$, 650 | 32% at 2000 nM | |
| M | FABMS, MH$^+$, 676.4 | >2000 nM | |
| O | FABMS, MH$^+$, 652 | >2000 nM | |
| P | FABMS, MH$^+$, 667 | >2000 nM | 0.22 |
| Q | FABMS, MH$^+$, 674.6 | 42% at 500 nM | |
| R | FABMS, MH$^+$, 700.4 | >2000 nM | |
| S | FABMS, MH$^+$, 701.5 | 1250 nM | |
| T | FABMS, MH$^+$, 675.4 | 1800 nM | |

Using the above biological assay, (Test 1), compound U of the invention was found to have an IC$_{50}$ equal to 38 µM which demonstrates that this compound has activity against retroviruses including HIV; and also inhibits the action of renin and is therefore believed to active against hypertension. As used in the above table, * means that the same measurement was taken twice and both measurements are given; and FABMS means fast atom bombardment mass spectrogram. As indicated in the table above, certain of the mass spectrograms are done with hydrogen, and others are done with sodium.

Additional compounds of the invention have the following boiological activities:

| Compound | Physcal Data | SPA IC$_{50}$ (nM) | Cells IC$_{50}$ (µg/ml) |
|---|---|---|---|
| W or X (isomer A) | FABMS, MH$^+$, 656 | 70 | |
| W or X (isomer B) | FABMS, MH$^+$, 656 | 52 | |
| Y | FABMS, MH$^+$, 624 | 365 | 3.2 |
| Z | FABMS, MH$^+$, 700.4 | 160 | |
| AA | FABMS, MH$^+$, 653.2 | 280 | 3.2 |

Blank spaces in the above tables indicate that the compound has not been tested in that particular assay.

The IC$_{50}$s above indicate that the compounds of formula I are active against HIV and are therefore useful in treating AIDS.

The compounds of this invention can be administered in any number of conventional dosage forms, e.g., oral, parenteral, rectal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, solubilizing agents, emulsifying agents, dispersing agents, suspending agents, perfumes, preservatives, lubricants, etc.

The compounds of this invention may be administered by any conventional mode of administration by employing an antiviral effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

The dosage to be administered and the route of administration depends upon the particular compound used, the age and general health of the patient and the severity of the viral condition. Thus, the dose ultimately decided upon must be left to the judgment of a trained health-care practitioner.

The compounds of this invention may also be administered concurrently with other known anti-viral agents such as AZT. The compounds of this invention may also be administered either before or after the administration of other known antiviral agents such as AZT. The just above mentioned combination therapies is believed to result in a synergistic action between the particular compound of the invention, and the other anti-HIV agent administered.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

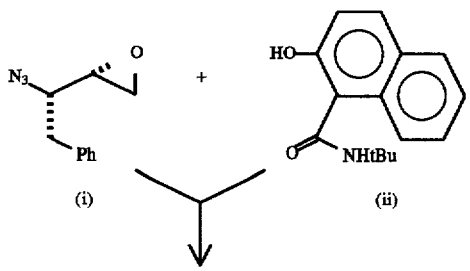

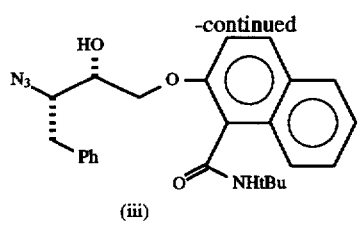

(iii)

1.803 g of the azide (i) was reacted with 2.550 g of the naphthol (ii) in DMF (20 ml) at a temperature of 120° C. for 16 hours. After aqueous work-up and column chromatography of the reaction mixture, 0.6778 g of the desired product (iii) was obtained.

EXAMPLE 2

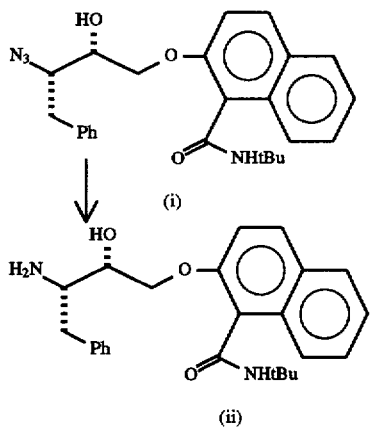

1.521 g of the azide (i) was hydrogenated under 1 atmosphere of hydrogen using the hydrogenation catalyst 10% palladium on carbon (0.40 g) and in the solvent ethanol (15 ml). The reaction was filtered through a pad of Celite and the filtrate concentrated under reduced pressure. Column chromatography of the crude reaction product gave 0.973 g of the amino alcohol (ii).

EXAMPLE 3

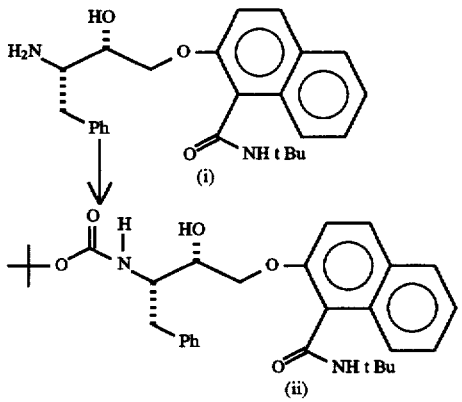

Triethylamine (175 microliters) was added dropwise to a stirred solution of the amine (i) (0.4248 g) and di-tert-butylpyrocarbonate (0.251 g) in dioxane (50 ml) at room temperature under an atmosphere of nitrogen. The resulting mixture was stirred overnight, concentrated and purified by column chromatography on silica gel using ethyl acetate/hexane (1:1) as the eluant to give 0.423 g of carbamate (ii).

EXAMPLE 4

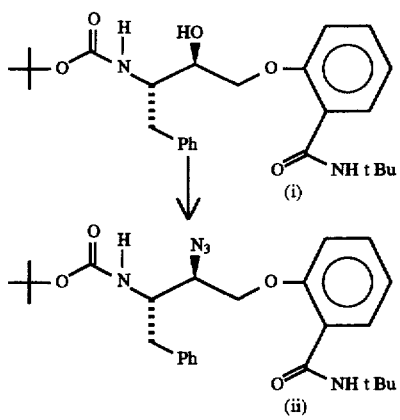

Triethylamine (124 microliters) was added a dropwise to a stirred solution of the alcohol (i) (0.2708 g) and mesylchloride (51 microliters) in dichloromethane (5 ml) at room temperature. The resulting mixture was stirred for 3 hours, partitioned between ethyl acetate and water. The organic phase was separated, washed twice with water, and concentrated to give the mesylate (ii) 0.306 g as a white solid.

EXAMPLE 5

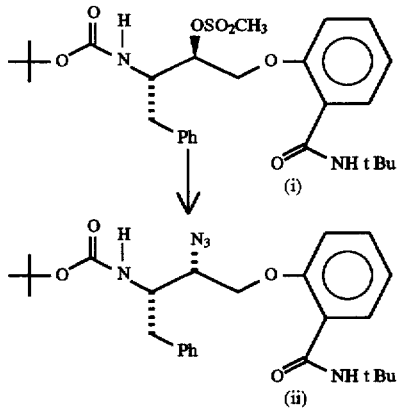

0.1347 g of sodium azide was added to a stirred solution of the mesylate 0.9226 g (i) in DMF (10 ml) and the resulting mixture was heated to 90° C. for 3 hours. After cooling, the mixture was partitioned between ethyl acetate and water and worked up. Column chromatography of the crude reaction mixture gave azide (ii) 0.791 g, as a white solid.

EXAMPLE 6

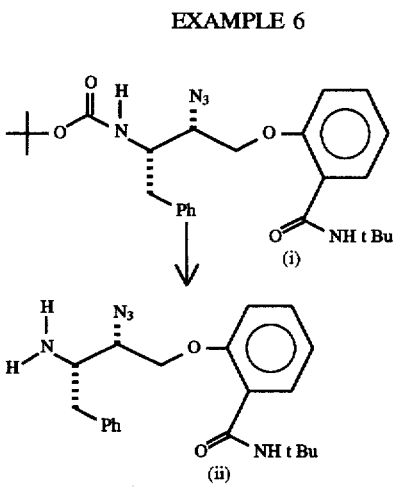

3 ml of trifluoroacetic acid (TFA) was added to a stirred solution of 0.1379 g of carbamate (i) in 3 ml of dichloromethane, cooled in an ice bath under an atmosphere of nitrogen. The mixture was stirred for 3 hours and the volatiles were removed under reduced pressure. The residue was dissolved in ethyl acetate, and excess triethylamine was added. After washing three times with brine, the organic phase was dried and concentrated to give 0.101 g of the azido amine (ii).

EXAMPLE 7

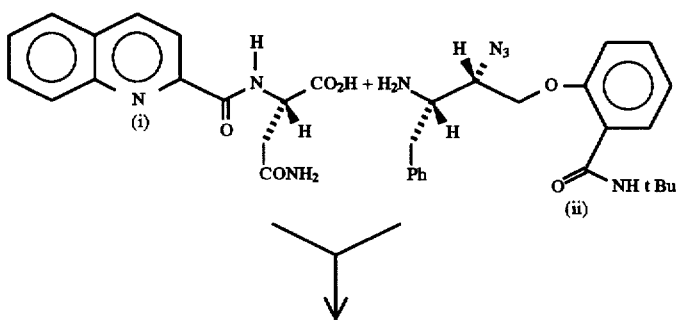

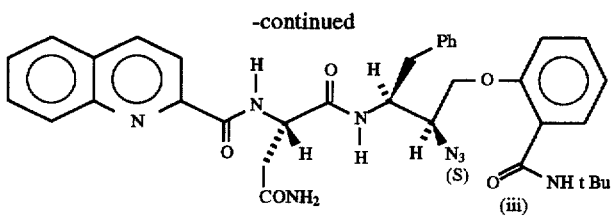

Triethylamine (2×37 microliters) was added in two portions ( about ½ hour apart) to a stirred solution of the amine (ii) (0.1020 g), the acid (i) (76.8 mgs) and BOP reagent (0.1302 g) in CH₂Cl₂ (2 ml). When the addition was complete the resulting mixture was stirred for 3 hours, and partitioned between ethyl acetate and water. Aqueous workup and column chromatography of the crude reaction product on silica gel using EtOAc as eluant gave the desired adduct (iii) (35 mgs).

EXAMPLE 8

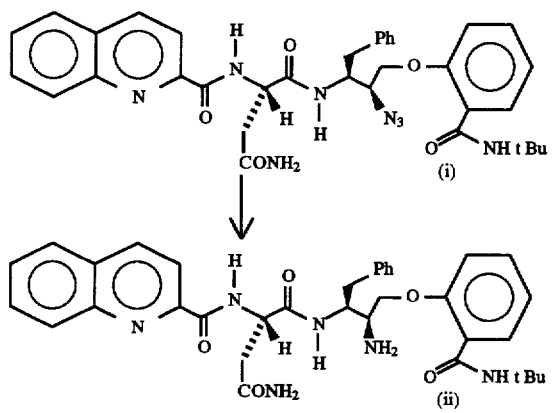

A suspension of 28.2 mg of azide (i), and 14 mgs of the catalyst 10% palladium on carbon in 2 ml of ethanol were placed under an atmosphere of hydrogen at room temperature over night. The crude reaction product was filtered through a pad of Celite and the solid washed thoroughly with ethyl acetate. The combined filtrate was concentrated and the crude reaction product was purified by plate chromatography using ethyl acetate:methanol:triethylamine; 85:10:5 as the eluant to give 18 mg of the amine (ii) as a yellow solid.

EXAMPLE 9

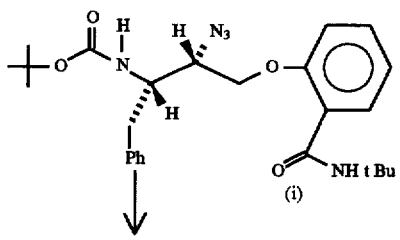

A suspension of 92 mg of the azide (i) and 10% Pd—C (46 mgs) was stirred under an atmosphere of hydrogen overnight. The mixture was filtered through a pad of Celite and washed thoroughly with ethyl acetate. The filtrate was concentrated to yield 82.3 mg of amine (ii) as colorless oil.

EXAMPLE 10

20 mg of acetylchloride was added dropwise to a stirred solution of 0.1031 g of amine (i) in 5 ml of pyridine at room temperature. The resulting mixture was stirred for a period of 3 hours under an atmosphere of nitrogen and then partitioned between 5% HCl and ethyl acetate. After a standard aqueous workup and purification of the crude reaction product by column chromatography on silica gel using ethyl acetate-hexane (7:3) as the eluant, crude amide (ii) in the amount of 56.4 mgs was obtained as a white solid.

EXAMPLE 11

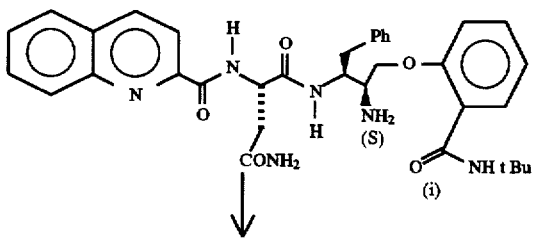

-continued

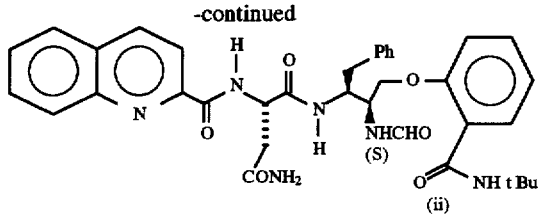

6.6 mgs of p-nitrophenyl formate was added to a stirred solution of 22.4 mgs of the amine (i) and 7 microliters of diisopropylethyl amine in 2 ml of DMF. The resulting mixture was stirred overnight at room temperature, partitioned between ethyl acetate and water. Aqueous workup and purification of the crude reaction product by column chromatography on silica gel using ethyl acetate/methanol (10:1) as the eluant gave the desired formamide (ii) (15.8 mg) as a white solid. FABMS MH⁺, 653.2.

EXAMPLE 12

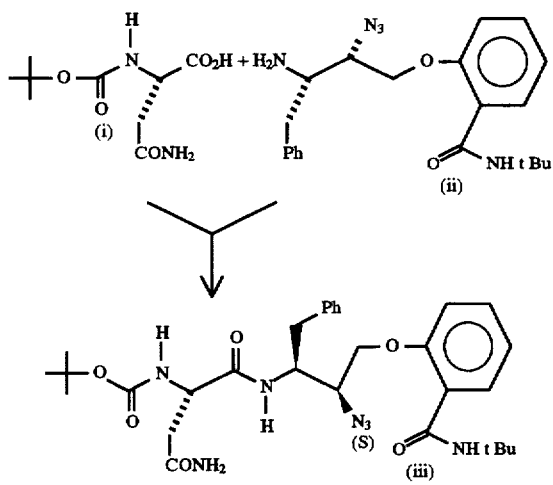

Triethylamine (2×0.73 ml) was added in two portions (about ½ hour apart) to a stirred solution of the amine (ii) (1.99 g), the acid (i) (1.33 g) and BOP reagent (2.54 g) in CH₂Cl₂ (20 ml). When the addition was complete the resulting mixture was stirred for 3 hours, and partitioned between ethyl acetate and water. Aqueous work-up and column chromatography of the crude reaction product on silica gel using EtOAc as eluant gave the desired adduct (iii) (1.327 g).

EXAMPLE 13

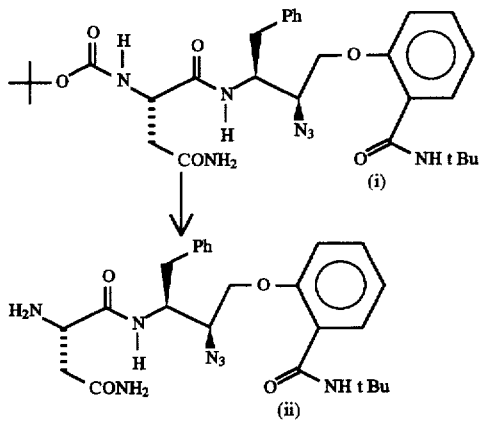

20 ml of trifluoroacetic acid (TFA) was added to a stirred solution of 1.209 g of carbamate (i) in 20 ml of dichloromethane, cooled in an ice bath under an atmosphere of nitrogen. The mixture was stirred for 3 hours and the volatiles were removed under reduced pressure. The residue was dissolved in ethyl acetate, and excess triethylamine was added. After washing three times with brine, the organic phase was dried and concentrated to give 1.009 g of the azido amine (ii) as a white solid.

EXAMPLE 14

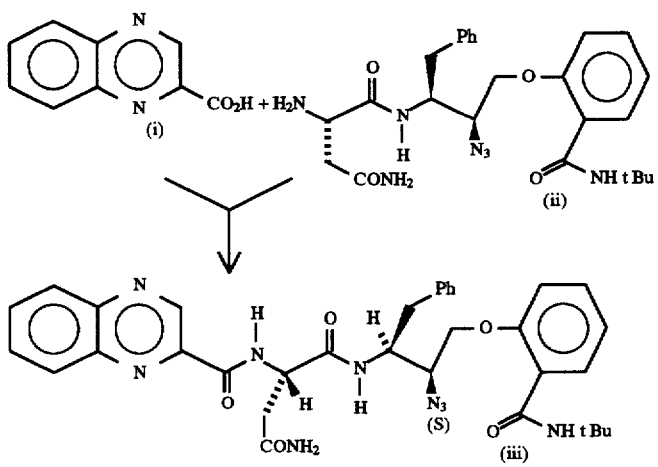

Triethylamine (2×31 microliters) was added in two portions (about ½ hour apart) to a stirred solution of the amine (ii) (99.5 mg), the acid (i) (38.4 mg) and BOP reagent (97.8 mg) in CH₂Cl₂ (5 ml). When the addition was complete the resulting mixture was stirred for 3 hours, and partitioned between ethyl acetate and water. Aqueous work-up and column chromatography of the crude reaction product on silica gel using EtOAc as eluant gave the desired adduct (iii) (0.1133 g) as a white solid.

and water. Aqueous work-up and column chromatography on silica gel using EtOAc-hexane (7:3) gave desired product (iii) 39.4 mgs as a white solid.

EXAMPLE 15

EXAMPLE 16

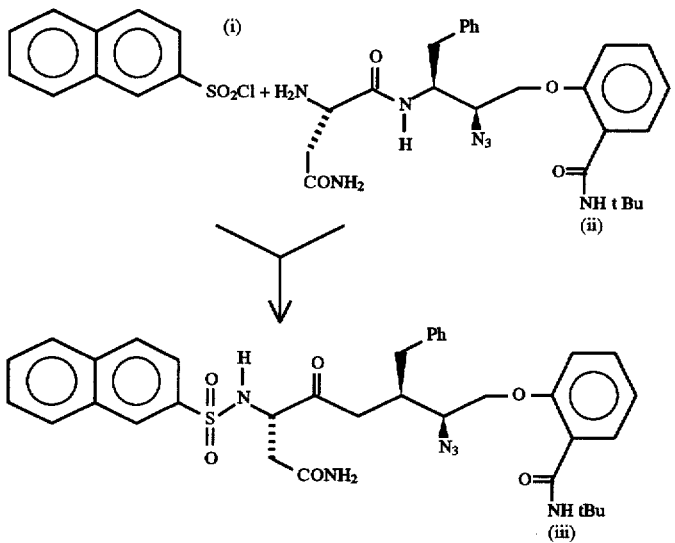

Triethylamine (27 microliters) was added dropwise to a stirred solution of the amine (ii) (94.8 mg) and sulfonyl chloride (i) (47.8 mg) in dichloromethane (4 ml) at room temperature under an atmosphere of nitrogen. The reaction

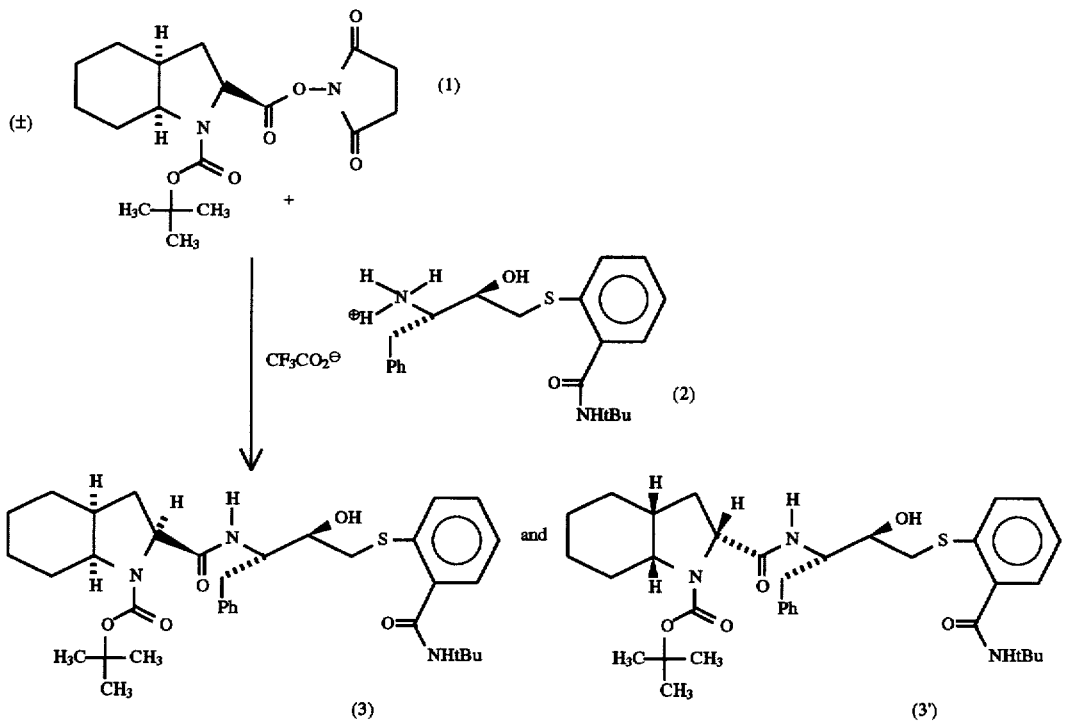

mixture was stirred for 3 hours, partitioned between EtOAc

Triethylamine (46 µl; 32.2 mg) was added to a stirred solution of the racemic ester (1) (54.4 mgs; 0.15 mmol) and salt (2) (72.5 mgs; 0.15 mmol) in dichloromethane (1 mL), at room temperature, under an atmosphere of nitrogen. The resulting mixture was stirred overnight, filtered and the filtrate purified by plc using ethyl acetate:hexane (1:1) as the eluant to give the stereoisomeric mixture of peptides (3) and (3') (58.5 mgs; 63%) as a white solid. The starting materials used in the above example are either known or may be prepared by known methods.

Physical data for the final product of this example just above is as follows: FAB MS MH$^+$ 624.2. The final product of this example just above, which is designated as compound U, may also exhibit anti-fungal, anti-bacterial and/or anti-inflammatory activity. The same properties may also be possessed by other compounds of formula U'.

Compound A was made by procedures analogous to those set forth in Examples 4, 5, 6, 7, and 8.

Compound D was made by procedures analogous to those set forth in Examples 4, 5, 6, 8, 12, 13 and 14.

Compound E was made by procedures analogous to those set forth in Examples 4, 5, 6, 12, 13 and 14.

Compound F was made by procedures analogous to those set forth in the Examples given for the preparation of Compound D.

Compound G was made by procedures analogous to those set forth in the Examples given for the preparation of Compound E.

Compound H was made by procedures analogous to those set forth in the Examples given for the preparation of Compound D.

Compound I was made by procedures analogous to those set forth in the Examples given for the preparation of Compound E.

Compound J was made by procedures analogous to those set forth in Examples 4, 5, 6, 8, 1 2, 13 and 15.

Compound K was made by procedures analogous to those set forth in Examples 4, 5, 6, 12, 13 and 15.

Compound L was made by procedures analogous to those set forth in the Examples given for the preparation of Compound D.

Compound M was made by procedures analogous to those set forth in the Examples given for the preparation of Compound E.

Compound O was made by procedures analogous to those set forth in the Examples given for the preparation of Compound E.

Compound P was made by procedures analogous to those set forth in Examples 3, 7, 9 and 10.

Compound Q was made by procedures analogous to those set forth in Examples 1, 2, 3, 4, 5, 6, 7 and 8.

Compound R was made by procedures analogous to those set forth in Examples 1, 2, 3, 4, 5, 6, and 7.

Compound S was made by procedures analogous to those set forth in Examples 1, 2, 3, 4, 5, 6, and 7.

Compound T was made by procedures analogous to those set forth in Examples 1, 2, 3, 4, 5, 6, 7 and 8.

Compound N can be made by procedures analogous to those set forth in this specification.

EXAMPLE 17

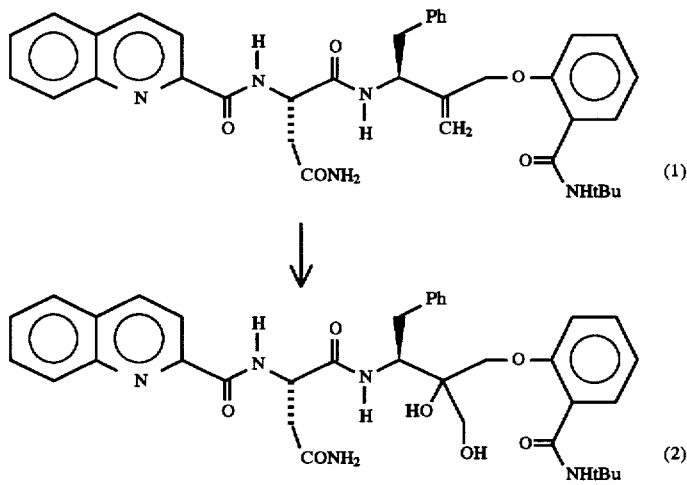

8.5 mg of $K_2CO_3$ and 25.9 mg of $K_2Fe(CN)_6$ and 1.9 mg potassium osmate were added in order to a stirred solution of 31.7 mg of the alkene (1) in 1 ml of t-BuOH and 1 ml of $H_2O$. The reaction was stirred over night. Thin layer chromatography (tlc) indicated that the reaction was not complete so a further portion of 8.5 mg of $K_2CO_3$ and 25.9 mg of $K_2Fe(CN)_6$ and 1.9 mg potassium osmate were added. After stirring for a further 3 hours, sodium sulfate was added and stirred for a further 1 hour. Aqueous work-up and plate chromatography on selica gel using EtOAc as the eluant gave: (1) a non-polar isomer (isomer A) (6.3 mgs) as a white solid, MH$^+$, 656; and (2) a polar isomer (isomer B) (5.1 mgs) as a white solid FABMS MH$^+$, 656.

EXAMPLE 18

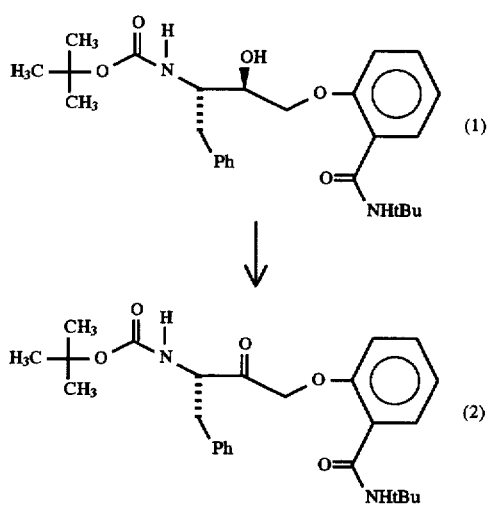

2.518 g of chromium trioxide was added to a stirred mixture of pyridine (4.07 ml) and acetone (150 ml), cooled in an ice bath. The dark suspension was stirred for 15 minutes then alcohol (1) (2.30 g) in acetone (20 ml) was added. The mixture was slowly warmed to room temperature and the reaction stirred at room temperature for 1 week. Aqueous work-up and column chromatography on silica gel using EtOAc-hexane (3:7) as eluant gave the ketone (2) (0.712 g; 31%) as a white solid; and recovered alcohol (1) (59%) a white solid.

EXAMPLE 19

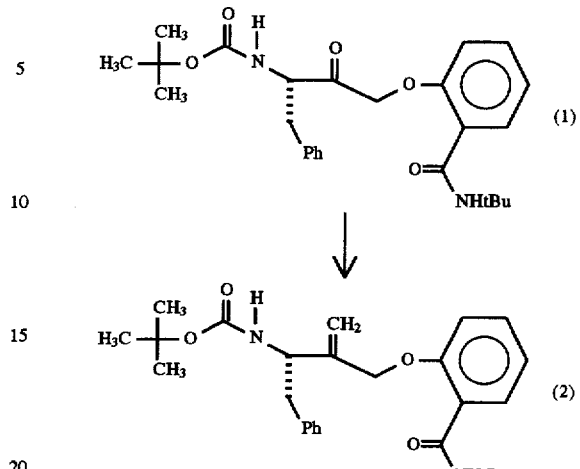

6.0 ml of a 1.0M solution of sodium hexamethyldisilazide (NaHMDS) was added dropwise to a stirred suspension of 2.519 g of methyl triphenylphosphonium bromide in tetrahydrofuran (THF) (50 ml) under an atmosphere of nitrogen. The resulting orange solution was stirred for ½ hour, cooled to −78° C. stirred for a further ½ hour, and a THF (10 ml) solution of 0.5487 g (1.2 mmol) of ketone (1) was added. A total of 60 ml of THF was used for the entire reaction. After stirring at −78° C. for about one and a half hours, the reaction was allowed to warm slowly to room temperature. Aqueous work-up and column chromatography of the crude reaction product using EtOAc-hexane (1:4) gave the desired alkene (2) (0.344 g).

EXAMPLE 20

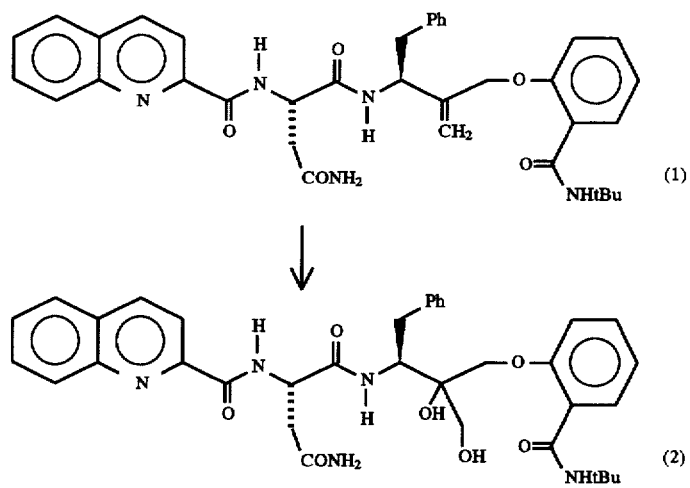

39.5 mg of the AD-mix-α was added to the stirred solution of ½ ml of t-BuOH and ½ ml of water and the resulting mixture was stirred overnight. Tlc indicated that no reaction was occurring 2.7 mg of methane sulfonamide was added and stirred for a further 3 hours and still no reaction was indicated. 5 mg of chiral ligand present in AD-mix-α was added stirred for a further 15 minutes. After stirring for 3 hours Tlc indicated that the reaction was complete. Sodium sulfite was added and the suspension was stirred for 1 hour before partitioning between EtOAc and water. Aqueous workup on plate chromatography and silica gel; using EtOAc-MeOH (20:1) as the eluant gave the diol (2) 9.0 mg as a white solid. FABMS MH⁺, 656 (17.5 mg)

EXAMPLE 21

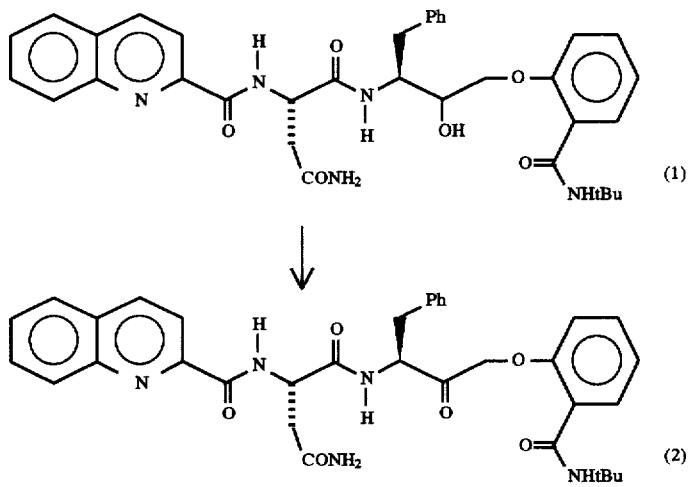

0.3309 g chromium trioxide was added to a mixture of pyridine (535 µl) in acetone (10 ml) and stirred at room temperature for 15 minutes and then an acetone (10 ml) solution of 0.4137 g of alcohol was added and the resulting mixture was stirred for 10 days. Aqueous work-up and purification of the crude reaction product on silica gel (column chromatography) using Et OAc-MeOH (20:1) as eluant gave ketone (2), 0.1776 g, as a white solid and recovered starting material (0.1913 g). FABSMH⁺, 624

What is claimed is:

1. A compound of the formula

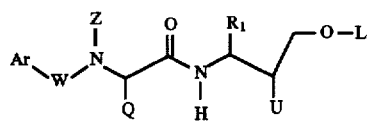 I wherein Ar is

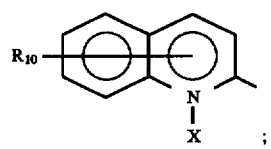

$R_{10}$ is H or OH;
X is an electron pair;
W is

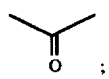 ;

Q is

CONH₂;

$R_1$ is

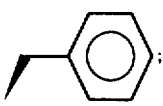 ;

Z is H;

U is

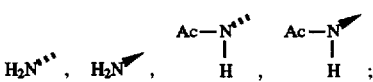

and Ac is formyl;

L is

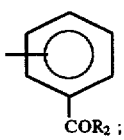
COR₂ ;

$R_2$ is

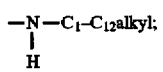

an epimer or racemate thereof, or a pharmaceutically acceptable salt thereof.

2. A compound according to claim 1, wherein W is CO.

3. A compound according to claim 1, wherein Q is

CONH₂.

4. A compound according to claim 1, wherein R₁ is

5. A compound according to claim 1, wherein U is

NH₂.
(S)

6. A compound according to claim 1, wherein —O-L is

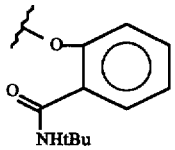

7. A pharmaceutical composition comprising a compound according to claim 1, in combination with a pharmaceutically acceptable carrier.

8. A method for treating HIV which comprises administering to a patient in need of such treatment an anti-HIV effective amount of a compound according to claim 1.

9. A compound according to claim 1 of the formula

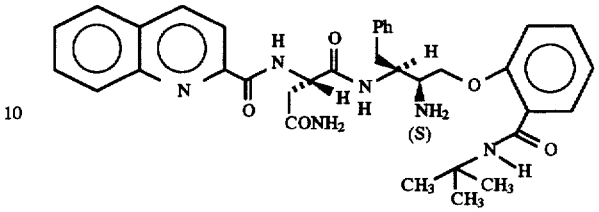

or a pharmaceutically acceptable salt thereof.

10. A compound according to claim 1 of the formula

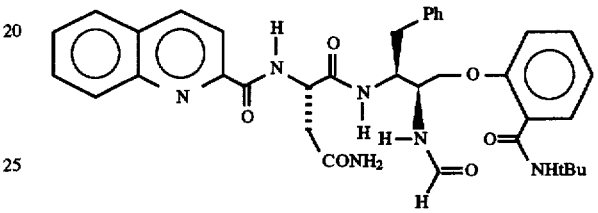

or a pharmaceutically acceptable salt thereof.

* * * * *